United States Patent
Pimentel et al.

(10) Patent No.: US 12,411,127 B2
(45) Date of Patent: Sep. 9, 2025

(54) MEASUREMENT OF HYDROGEN SULFIDE DURING BREATH TESTING

(71) Applicant: Cedars-Sinai Medical Center, Los Angeles, CA (US)

(72) Inventors: Mark Pimentel, Los Angeles, CA (US); Kapil Gupta, Los Angeles, CA (US); Ali Rezaie, West Hollywood, CA (US); Nipaporn Pichetshote, Los Angeles, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 915 days.

(21) Appl. No.: 16/487,645

(22) PCT Filed: Feb. 23, 2018

(86) PCT No.: PCT/US2018/019490
§ 371 (c)(1),
(2) Date: Aug. 21, 2019

(87) PCT Pub. No.: WO2018/156937
PCT Pub. Date: Aug. 30, 2018

(65) Prior Publication Data
US 2020/0064330 A1 Feb. 27, 2020

Related U.S. Application Data

(60) Provisional application No. 62/589,484, filed on Nov. 21, 2017, provisional application No. 62/502,350, (Continued)

(51) Int. Cl.
*B01L 3/00* (2006.01)
*A61K 31/437* (2006.01)
(Continued)

(52) U.S. Cl.
CPC ......... *G01N 33/497* (2013.01); *A61K 31/437* (2013.01); *G01N 33/4975* (2024.05); *G01N 2800/065* (2013.01); *G01N 2800/52* (2013.01)

(58) Field of Classification Search
CPC ......... G01N 33/497; G01N 2033/4975; G01N 2800/065; G01N 2800/52; G01N 33/84; A61K 31/437
See application file for complete search history.

(56) References Cited

U.S. PATENT DOCUMENTS 5,291,898 A 3/1994 Wolf
6,364,938 B1 4/2002 Birbara et al.
(Continued)

FOREIGN PATENT DOCUMENTS

AU 2016315721 A1 8/2022
BR 11-2018-004097 A2 4/2018
(Continued)

OTHER PUBLICATIONS

Supplementary European Search Report for EP 18758133 dated Feb. 1, 2021.
(Continued)

*Primary Examiner* — Jennifer Wecker
*Assistant Examiner* — Oyeleye Alexander Alabi
(74) *Attorney, Agent, or Firm* — Linda B. Huber; Nixon Peabody LLP

(57) ABSTRACT

Described herein are methods of detecting levels hydrogen sulfide ($H_2S$) to diagnose $H_2S$ positive disease or conditions. Examples of $H_2S$ positive diseases and conditions include small intestinal bacterial overgrowth, diarrhea, fatigue, bowel urgency and abdominal pain. The $H_2S$ level can guide treatments for subjects who have high levels of $H_2S$.

4 Claims, 10 Drawing Sheets

Related U.S. Application Data filed on May 5, 2017, provisional application No. 62/463,175, filed on Feb. 24, 2017.

(51) Int. Cl.
| | |
|---|---|
| B01F 33/302 | (2022.01) |
| B01F 33/3033 | (2022.01) |
| B01L 7/00 | (2006.01) |
| B01L 9/00 | (2006.01) |
| B65G 47/80 | (2006.01) |
| B82Y 20/00 | (2011.01) |
| B82Y 30/00 | (2011.01) |
| B82Y 40/00 | (2011.01) |
| C12M 1/34 | (2006.01) |
| C12M 3/06 | (2006.01) |
| C12N 1/14 | (2006.01) |
| C12N 1/20 | (2006.01) |
| C12Q 1/02 | (2006.01) |
| C12Q 1/6806 | (2018.01) |
| C12Q 1/6844 | (2018.01) |
| C12Q 1/6848 | (2018.01) |
| C12Q 1/686 | (2018.01) |
| G01N 15/10 | (2024.01) |
| G01N 15/14 | (2024.01) |
| G01N 15/1433 | (2024.01) |
| G01N 21/29 | (2006.01) |
| G01N 21/65 | (2006.01) |
| G01N 33/497 | (2006.01) |
| G01N 33/543 | (2006.01) |
| G01N 33/557 | (2006.01) |
| G01N 33/574 | (2006.01) |
| G01N 33/58 | (2006.01) |

(56) References Cited

U.S. PATENT DOCUMENTS

| | | | |
|---|---|---|---|
| 6,805,852 | B2 | 10/2004 | Lin et al. |
| 6,861,053 | B1 | 3/2005 | Lin et al. |
| 7,048,906 | B2 | 5/2006 | Lin et al. |
| 7,056,686 | B2 | 6/2006 | Lin et al. |
| 7,288,136 | B1 | 10/2007 | Gray et al. |
| 7,452,857 | B2 | 11/2008 | Lin et al. |
| 7,585,838 | B2 | 9/2009 | Lin et al. |
| 7,605,240 | B2 | 10/2009 | Lin et al. |
| 7,718,608 | B2 | 5/2010 | Lin et al. |
| 7,736,622 | B2 | 6/2010 | Lin et al. |
| 7,935,799 | B2 | 5/2011 | Lin et al. |
| 8,197,805 | B2 | 6/2012 | Lin et al. |
| 8,383,026 | B1 | 2/2013 | Luebke et al. |
| 8,500,854 | B1 | 8/2013 | Pennline et al. |
| 8,821,614 | B1 | 9/2014 | Albenze et al. |
| 9,050,579 | B1 | 6/2015 | Wickramanayake et al. |
| 9,066,962 | B2 | 6/2015 | Pimentel et al. |
| 9,186,854 | B1 | 11/2015 | Luebke et al. |
| 9,192,618 | B2 | 11/2015 | Pimentel et al. |
| 9,358,245 | B2 | 6/2016 | Pimentel et al. |
| 10,066,254 | B2 | 9/2018 | Pimentel et al. |
| 10,844,417 | B2 | 11/2020 | Pimentel et al. |
| 11,103,157 | B2 | 8/2021 | Gupta et al. |
| 2004/0147038 | A1 | 7/2004 | Lewis et al. |
| 2006/0074335 | A1 | 4/2006 | Ben-Oren et al. |
| 2006/0182693 | A1 | 8/2006 | Kristiansen et al. |
| 2006/0246045 | A1 | 11/2006 | Pimentel et al. |
| 2008/0045825 | A1 | 2/2008 | Melker et al. |
| 2008/0138320 | A1 | 6/2008 | Pimentel et al. |
| 2008/0182291 | A1 | 7/2008 | Pimentel et al. |
| 2009/0233888 | A1* | 9/2009 | Lin .................. A61K 35/413 436/119 |
| 2010/0209507 | A1* | 8/2010 | Lin .................. A61K 31/201 436/119 |
| 2011/0009764 | A1 | 1/2011 | Lanier et al. |
| 2011/0023581 | A1 | 2/2011 | Chou et al. |
| 2012/0150056 | A1 | 6/2012 | Christman et al. |
| 2012/0234076 | A1 | 9/2012 | Rigas |
| 2012/0285320 | A1 | 11/2012 | Heald et al. |
| 2014/0206636 | A1 | 7/2014 | Lin et al. |
| 2014/0228431 | A1 | 8/2014 | Pimentel et al. |
| 2015/0032019 | A1* | 1/2015 | Acker .................. A61B 5/097 600/532 |
| 2015/0099713 | A1 | 4/2015 | Pimentel et al. |
| 2016/0018371 | A1* | 1/2016 | Acharya ........... G01N 33/0037 436/121 |
| 2018/0249929 | A1 | 9/2018 | Nakagawa et al. |
| 2018/0271404 | A1 | 9/2018 | Gupta et al. |
| 2019/0136286 | A1 | 5/2019 | Pimentel et al. |
| 2021/0177303 | A1 | 6/2021 | Pimentel et al. |

FOREIGN PATENT DOCUMENTS

| | | | |
|---|---|---|---|
| CA | 2996425 A1 | 3/2017 | |
| CL | 2018570 | 6/2018 | |
| CN | 101650351 A | 2/2010 | |
| CN | 108139384 A | 6/2018 | |
| EP | 1200828 B1 | 8/1999 | |
| EP | 2267445 A1 | 12/2010 | |
| EP | 3344995 A1 | 7/2018 | |
| IN | 201827007178 A | 2/2018 | |
| KR | 20180043832 A | 4/2018 | |
| MX | 2018002721 A | 4/2018 | |
| NZ | 740135 A | 7/2020 | |
| WO | WO 2002083926 A2 | 10/2002 | |
| WO | WO-2005103677 A1 * | 11/2005 | ........... G01N 31/223 |
| WO | WO 2017040546 A1 | 3/2017 | |
| WO | 2018156937 A1 | 8/2018 | |
| WO | 2021127027 A1 | 6/2021 | |

OTHER PUBLICATIONS

Eugenia et al., Measurement of Hydrogen Sulfide during Breath testing correlated to Patient Symptoms, Gastroenterology, 2017, vol. 152(5).
Singapura et al., Su1792 Factors Contributing to Indeterminate QuantiFERON-TB Gold In-Tube Test Results in Patients with Inflammatory Bowel Disease, Gastroenterology, 2016, vol. 150(4).
Bee et al., Hydrogen Sulfide in Exhaled Gases From Ventilated Septic Neonates and Children: A Preliminary Report, Pediatric Critical Care Medicine, 2017, vol. 18(8).
Zhang et al., Exhaled Hydrogen Sulfide Predicts Airway Inflammation Phenotype in COPD, 2014, vol. 60(2), pp. 251-258.
Rezaie et al., Hydrogen and Methane-Based Breath Testing in Gastrointestinal Disorders: The North American Consensus, the American Journal of Gastroenterology, 2017, pp. 1-10.
Cloarec et al., Breath hydrogen response to lactulose in healthy subjects: relationship to methane producing status. Gut, Mar. 1, 1990, vol. 31, No. 3, pp. 300-304.
Supplementary Search Report of SG 11201801664P, dated Jan. 17, 2020, 3 pages.
Ajibola et al., Effects of dietary nutrients on volatile breath metabolites, Journal of Nutritional Science, (Oct. 31, 2013), vol. 2, e34, pp. 1-15.
International Preliminary Report on Patentability for PCT/US2016/049528 dated Mar. 6, 2018, 7 pages.
International Search Report and Written Opinion for PCT/US2016/049528 dated Feb. 1, 2017, 13 pages.
International Search Report and Written Opinion of PCT/US2018/019490, dated Apr. 30, 2018, 9 Pages.
Partial Search Report of EP 16842833.2, dated Jan. 30, 2019, 17 pages.
Search Report and Written Opinion of SG 11201801664P, dated Mar. 28, 2019, 10 pages.
Supplemental Search Report of EP 16842833.2, dated Apr. 29, 2019, 16 pages.
Written Opinion with Translation of CL 201800570 dated Apr. 12, 2019, 33 pages.

(56) References Cited

OTHER PUBLICATIONS

Cowie et al., Membrane Inlet Ion Trap Mass Spectrometry for the Direct Measurement of Dissolved Gases in Ecological Samples, Journal of Microbiological Methods, 1999, vol. 35(1), pp. 1-12.
Lazik, D., Membrane Based Measurement Technology for in situ Monitoring of Gases in Soil, Sensors, 2009, vol. 9, pp. 756-767.
Lusk et al., Hydrogen Sulfide Monitoring Near Oil and Gas Production Facilities in Southeastern New Mexico and Potential Effects of Hydrogen Sulfide to Migratory Birds and Other Wildlife, 2010, U.S. Department of the Interior Fish & Wildlife Service Environmental Contaminants Program, 102 Pages.
Saad et al., Breath Tests for Gastrointestinal Disease: The Real Deal or Just a Lot of Hot Air?, Gastroenterology, 2007, vol. 133, pp. 1763-1766.
Scarlata, K., The Complete Idiot's Guide to Eating Well with IBS, New York, NY, Penguin Group, 2010.
Wang et al., Measurement of Mercury in Flue Gas Based on an Aluminum Matrix Sorbent, the Scientific World Journal, 2011, vol. 11, pp. 2469-2479.
Weaver et al., Incidence of Methanogenic Bacteria in a Sigmoidoscopy Population: an Association of Methanogenic Bacteria and Diverticulosis, 1986, Gut, vol. 27, pp. 698-704.
Lisowska et al., Small intenstine bacterial overgrowth is frequent in cystic fibrosis: combined hydrogen and methane measurements are required for its detection, Acta Biochimica Polonica, 2009, vol. 56(4), pp. 631-634.
Sachdeva et al., Small intestinal bacterial overgrowth (SIBO) in irritable bowel syndrome: frequency and predictors, Journal of Gastroenterology and Hepatology, 2011, vol. 26(3), pp. 135-138.
Brazilian Examination Report for BR112018004097 dated May 6, 2024, 8 pages.
Pimentel et al., Methanogens in human health and disease, American Journal of Gastroenterology supplements, 2012, 1:28-33.
Moraes do Nascimento, FLoT: an agent-bsed framework for self-adaptive and self-organizing internet of things aplications. Dissertation presented to the Programa Postgraduate course in Informatics of the Department of Information Technology at the Scientific Technical Center of PUC-Rio, Lucena, Rio de Janeiro, Aug. 2015, 102 pages.
Extended European Search Report for 20904094.8 dated Nov. 12, 2023, 9 pages.
Gouma et al., Sensing device for breath biomarker detection, 2019 IEEE International Symposium on Olfaction and Electronic Nose, May 26, 2019, pp. 1-3, XP033611802.
Singer-Englar et al., a novel 4-gas device for breath testing shows exhaled H2S is associated with diarrhea and abdominal pain in a large scale prospective trial, Gastroenterology, Elsevier Inc., US, 154(6), May 1, 2018, XP085389780, 1 page.

* cited by examiner

MEASUREMENT OF HYDROGEN SULFIDE DURING BREATH TESTING

CROSS-REFERENCE TO RELATED APPLICATIONS

This application is a National Phase of International Application No. PCT/US2018/019490 filed Feb. 23, 2018, currently pending, which designated the U.S. and that International Application was published under PCT Article 21(2) in English, which also includes a claim of priority under 35 U.S.C. § 119(e) to U.S. provisional patent application No. 62/463,175 filed Feb. 24, 2017, U.S. provisional patent application No. 62/502,350 filed May 5, 2017, U.S. provisional patent application No. 62/589,484 filed Nov. 21, 2017, the entirety of which is hereby incorporated by reference.

FIELD OF INVENTION

This invention relates to small intestinal bacterial overgrowth, irritable bowel syndrome and clinical symptoms such as diarrhea and fatigue.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The breath test (BT) is an important, noninvasive diagnostic test for small intestinal bacterial overgrowth (SIBO). BTs remain the simplest and most widely available evaluation in clinical practice. Presently, 3 gases are measured by this diagnostic modality including hydrogen ($H_2$), methane ($CH_4$) and carbon dioxide ($CO_2$), wherein the presence of detectable methane is notably correlated with constipation and the presence of detectable hydrogen is not demonstrated to correlate with any specific symptoms. Hydrogen sulfide ($H_2S$) gas is another microbial byproduct but is not included in the current measurement in BTs. Described herein, we examine the levels of detectable $H_2S$ from breath testing. In various embodiments, the levels of detectable $H_2S$ are used to determine associations with specific patient symptoms, and for treatment of $H_2S$ related conditions such as $H_2S$ positive SIBO, diarrhea, and fatigue.

SUMMARY OF THE INVENTION

The following embodiments and aspects thereof are described and illustrated in conjunction with compositions and methods which are meant to be exemplary and illustrative, not limiting in scope.

Various embodiments of the present invention provide for a method of treating a hydrogen sulfide ("$H_2S$") positive condition, comprising: administering a treatment for the $H_2S$ positive condition to a subject who has been diagnosed as having the $H_2S$ positive condition, wherein the $H_2S$ positive condition is selected from the group consisting of $H_2S$ positive small intestinal bacterial overgrowth ("SIBO"), $H_2S$ positive diarrhea, $H_2S$ positive fatigue, $H_2S$ positive bowel urgency, $H_2S$ positive abdominal pain and combinations thereof.

In various embodiments, the $H_2S$ positive condition can be diagnosed by a method comprising: obtaining a biological sample from the subject; measuring the $H_2S$ level in the biological sample; and diagnosing the $H_2S$ positive condition if the $H_2S$ level is higher than a reference level.

In various embodiments, the method can further comprise identifying the subject has having the $H_2S$ positive condition before administering the treatment for the $H_2S$ positive condition.

In various embodiments, the method can further comprise requesting a test result regarding the $H_2S$ positive condition before administering the treatment for the $H_2S$ positive condition, wherein the test result can be obtained from a method comprising: obtaining a biological sample from the subject; measuring the hydrogen sulfide ($H_2S$) level in the biological sample, and diagnosing the $H_2S$ positive condition if the $H_2S$ level is higher than a reference level, wherein the $H_2S$ positive condition can be selected from the group consisting of $H_2S$ positive small intestinal bacterial overgrowth ("SIBO"), $H_2S$ positive diarrhea, $H_2S$ positive fatigue, $H_2S$ positive bowel urgency, $H_2S$ positive abdominal pain and combinations thereof.

Various embodiments of the present invention provide for a method of detecting hydrogen sulfide ("$H_2S$") in a subject, comprising: obtaining a biological sample from the subject; measuring the hydrogen sulfide ($H_2S$) level in the biological sample; and comparing the $H_2S$ level to a reference level, wherein the subject is suspected to have a $H_2S$ positive condition selected from the group consisting of $H_2S$ positive small intestinal bacterial overgrowth ("SIBO"), $H_2S$ positive diarrhea, $H_2S$ positive fatigue, $H_2S$ positive bowel urgency, $H_2S$ positive abdominal pain and combinations thereof.

Various embodiments of the present invention provide for a method of diagnosing a hydrogen sulfide ("$H_2S$") positive condition, comprising: obtaining a biological sample from a subject; measuring the hydrogen sulfide ($H_2S$) level in the biological sample; and diagnosing $H_2S$ positive condition if the $H_2S$ level is higher than a reference level, wherein the $H_2S$ positive condition is selected from the group consisting of $H_2S$ positive small intestinal bacterial overgrowth ("SIBO"), $H_2S$ positive diarrhea, $H_2S$ positive fatigue, $H_2S$ positive bowel urgency, $H_2S$ positive abdominal pain and combinations thereof.

Various embodiments of the present invention provide for a method for selecting a therapy for a subject, comprising: obtaining a biological sample from a subject; measuring the hydrogen sulfide ($H_2S$) level in the biological sample; and selecting a therapy for an $H_2S$ positive condition if the $H_2S$ level is higher than a reference level, wherein the $H_2S$ positive condition is selected from the group consisting of $H_2S$ positive small intestinal bacterial overgrowth ("SIBO"), $H_2S$ positive diarrhea, $H_2S$ positive fatigue, $H_2S$ positive bowel urgency, $H_2S$ positive abdominal pain and combinations thereof.

Various embodiments of the present invention provide for a method for selecting a subject for a clinical trial, comprising: obtaining a biological sample from a subject; measuring the hydrogen sulfide ($H_2S$) level in the biological sample; and selecting the subject for a clinical trial for the treatment of an $H_2S$ positive condition if the $H_2S$ level is higher than a reference level, wherein the $H_2S$ positive condition is selected from the group consisting of $H_2S$ positive small intestinal bacterial overgrowth ("SIBO"), $H_2S$ positive diarrhea, $H_2S$ positive fatigue, $H_2S$ positive bowel urgency, $H_2S$ positive abdominal pain and combinations thereof.

In various embodiments, the treatment or therapy for these methods can be rifaximin.

In various embodiments, the biological sample in these methods can be a breath sample.

In various embodiments, the subject in these methods can have or be suspected of having irritable bowel syndrome.

In various embodiments, $H_2S$ can be measured in these methods using a four gas detection device or system and the four gases can be $H_2$, $CH_4$, $H_2S$, and $CO_2$.

In various embodiments, $H_2S$ can be measured in these methods after the subject ingests a controlled quantity of a substrate selected from the group consisting of lactulose, xylose, lactose, glucose, fructose and combinations thereof.

In various embodiments, the reference level in these methods can be 6 parts per million (ppm).

In various embodiments, the reference level in these methods can be 1.2 parts per million (ppm).

Other features and advantages of the invention will become apparent from the following detailed description, taken in conjunction with the accompanying drawings, which illustrate, by way of example, various features of embodiments of the invention.

DESCRIPTION OF THE INVENTION

Figure 1:
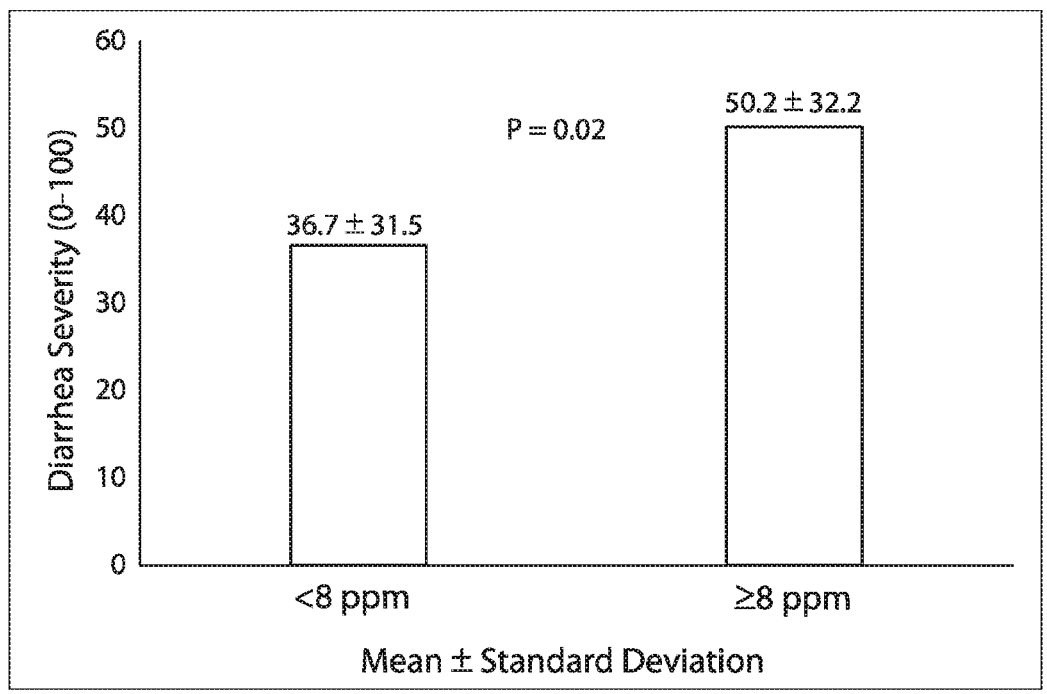
FIG. 1 depicts diarrhea severity in relation to hydrogen sulfide concentration. When the area under the curve (AUC) for $H_2S$ is ≥8 ppm there is a greater severity of diarrhea based on a 0-100 mm visual analogue scale.
Figure 2:
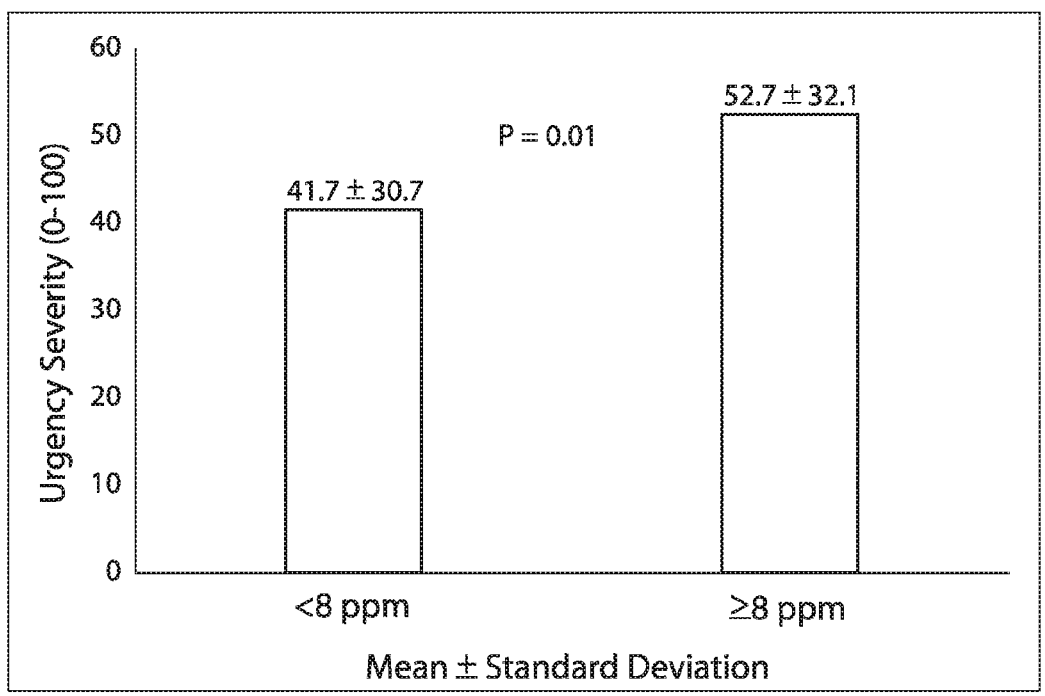
FIG. 2 depicts urgency severity in relation to hydrogen sulfide concentration. Similar to diarrhea, when the area under the curve (AUC) for $H_2S$ is ≥8 ppm there is a greater severity of urgency based on a 0-100 mm visual analogue scale. This provides internal consistency since urgency and diarrhea are related.
Figure 3:
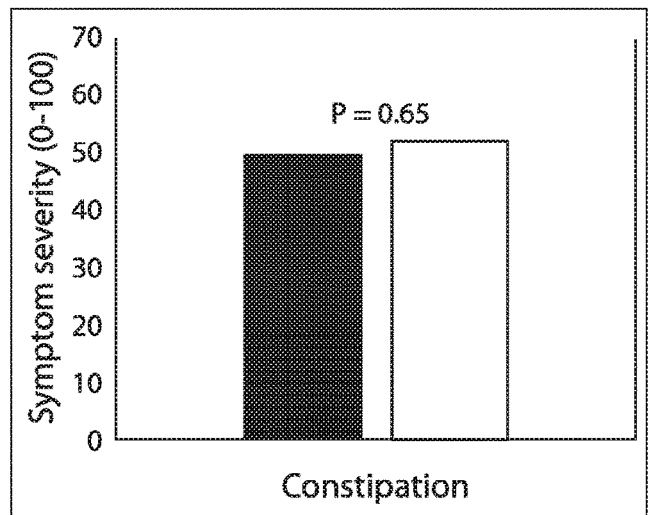
FIG. 3 depicts symptom severity (constipation) in relation to hydrogen sulfide concentration. Unlike diarrhea, $H_2S$ is not related to constipation.
Figure 4:
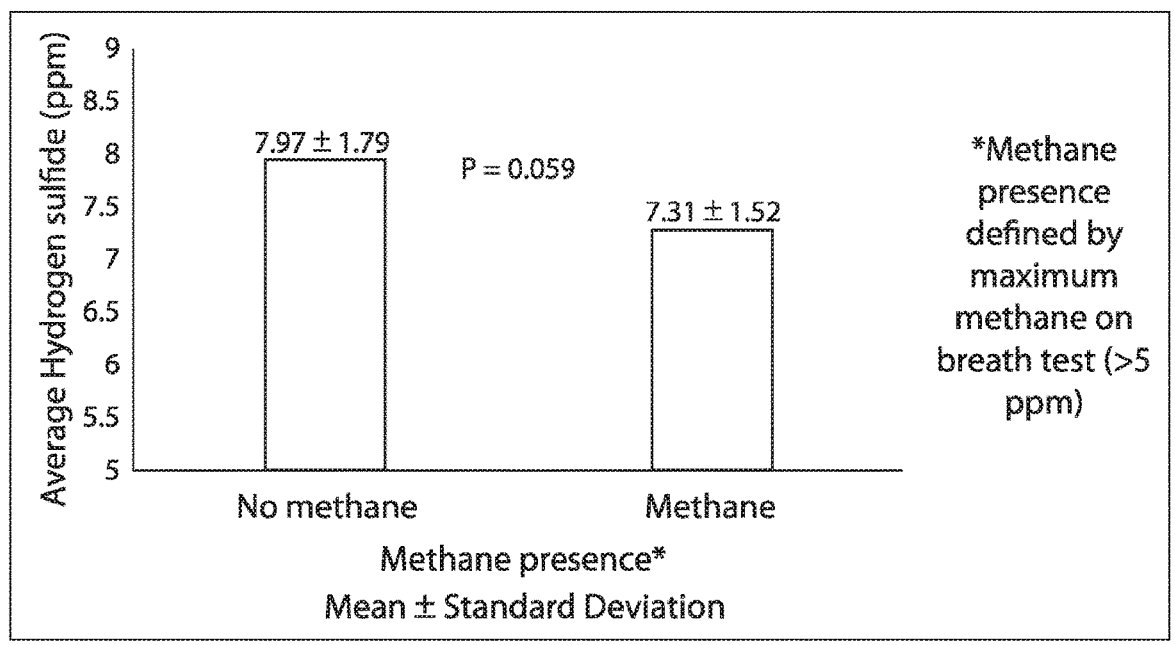
FIG. 4 depicts average hydrogen sulfide concentration in patients with or without breath methane. As $H_2S$ and $CH_4$ compete for hydrogen as a fuel source for production, it is evident that when there is higher $H_2S$, $CH_4$ is less and vice versa.
Figure 5:
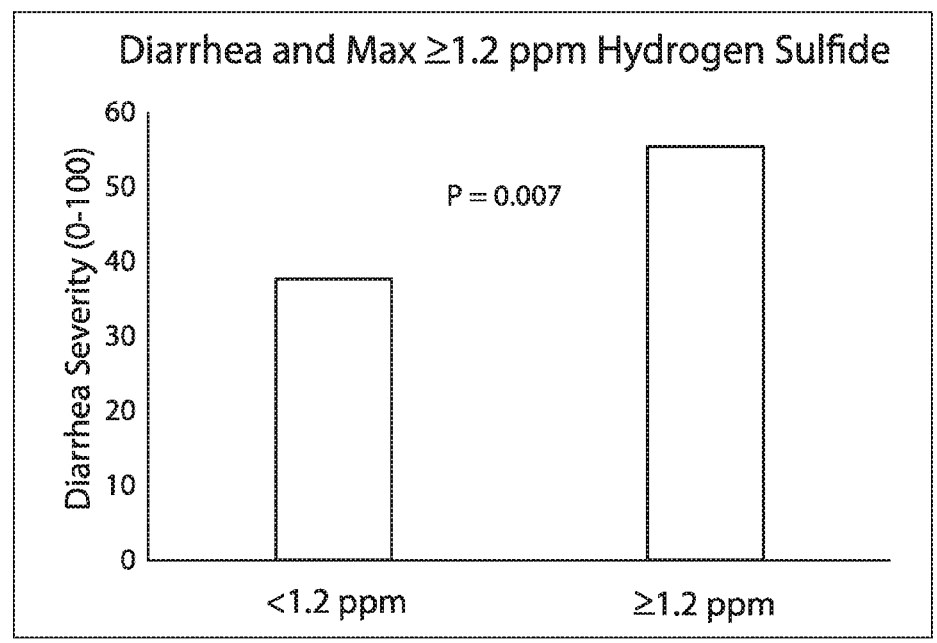
FIG. 5 depicts diarrhea severity in relation to hydrogen sulfide concentration cut-off set at 1.2 ppm. Another and perhaps better way to evaluate $H_2S$ is by peak value. As shown herein, peak $H_2S$ of ≥1.2 ppm was associated with diarrhea severity.
Figure 6:
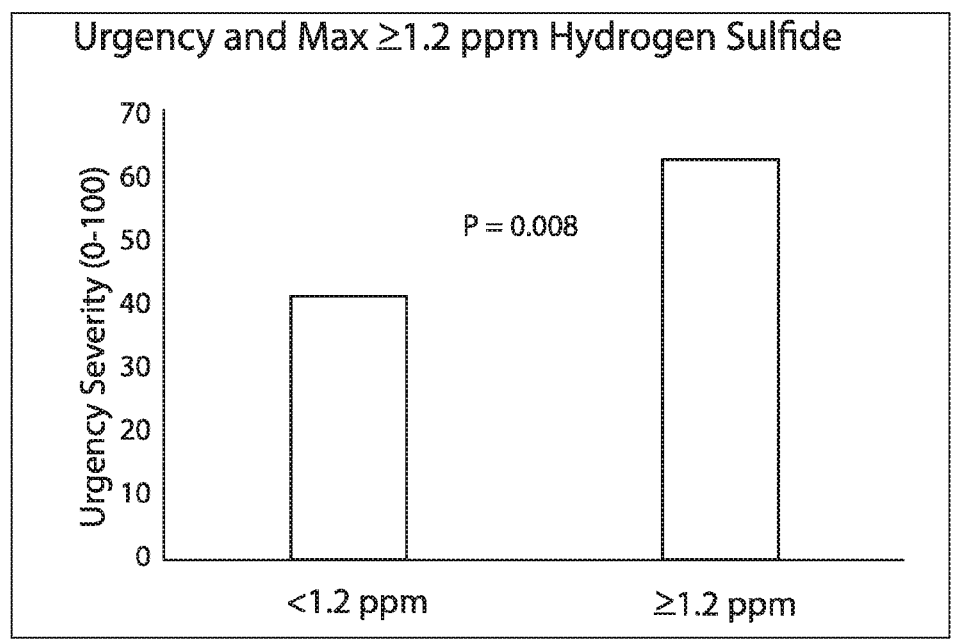
FIG. 6 depicts urgency severity in relation to hydrogen sulfide concentration cut-off set at 1.2 ppm. Another and perhaps better way to evaluate $H_2S$ is by peak value. As shown herein, peak $H_2S$ of ≥1.2 ppm was also associated with urgency severity.
Figure 7:
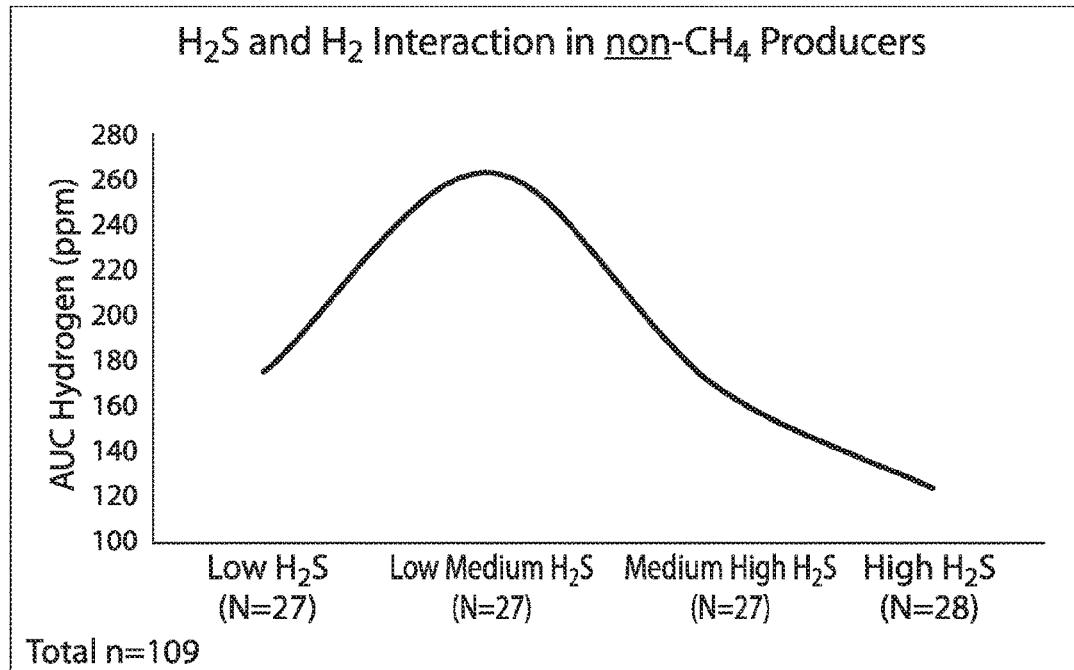
FIG. 7 depicts $H_2S$ and $H_2$ interaction in non-$CH_4$ Producers. In another way of examining the competition for hydrogen as a fuel source, this graph shows that when a breath test is normal, both $H_2S$ and $H_2$ are low. However, as $H_2S$ increases, the utilization of $H_2$ increases resulting in consumption represented by ever lower $H_2$ levels.
Figure 8:
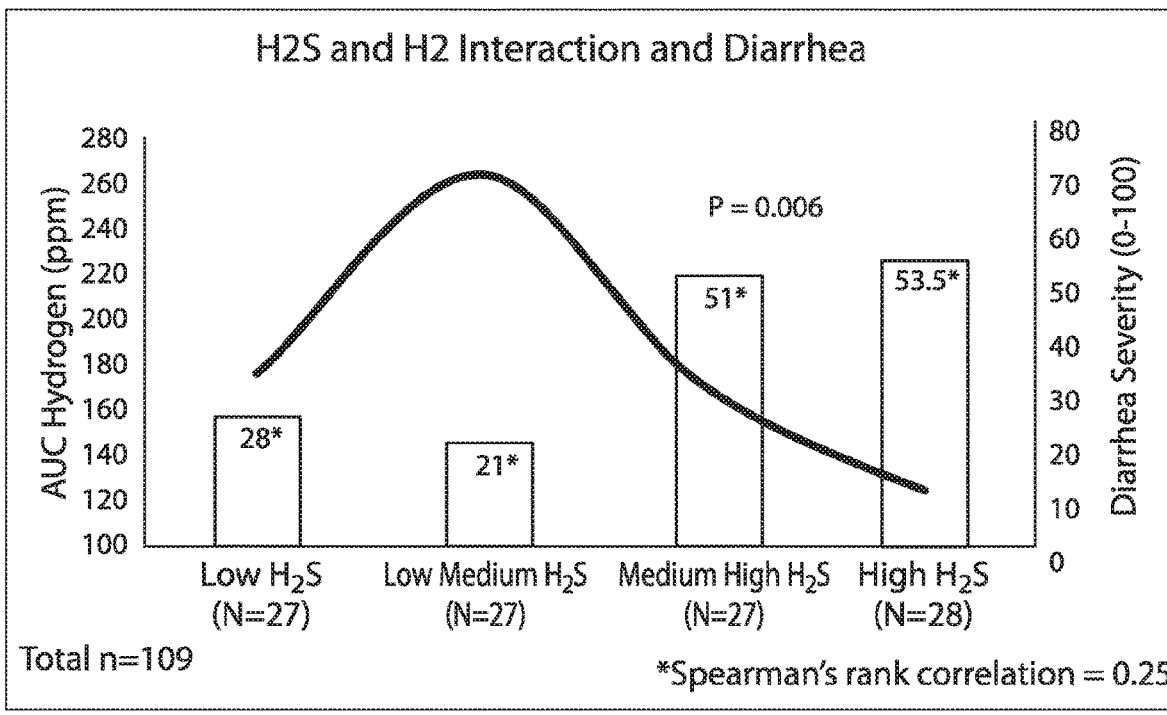
FIG. 8 depicts Hydrogen distribution by Hydrogen Sulfide. As the consumption of $H_2$ increases to create more $H_2S$ at the expense of $H_2$, there is ever increasing diarrhea.
Figure 9:
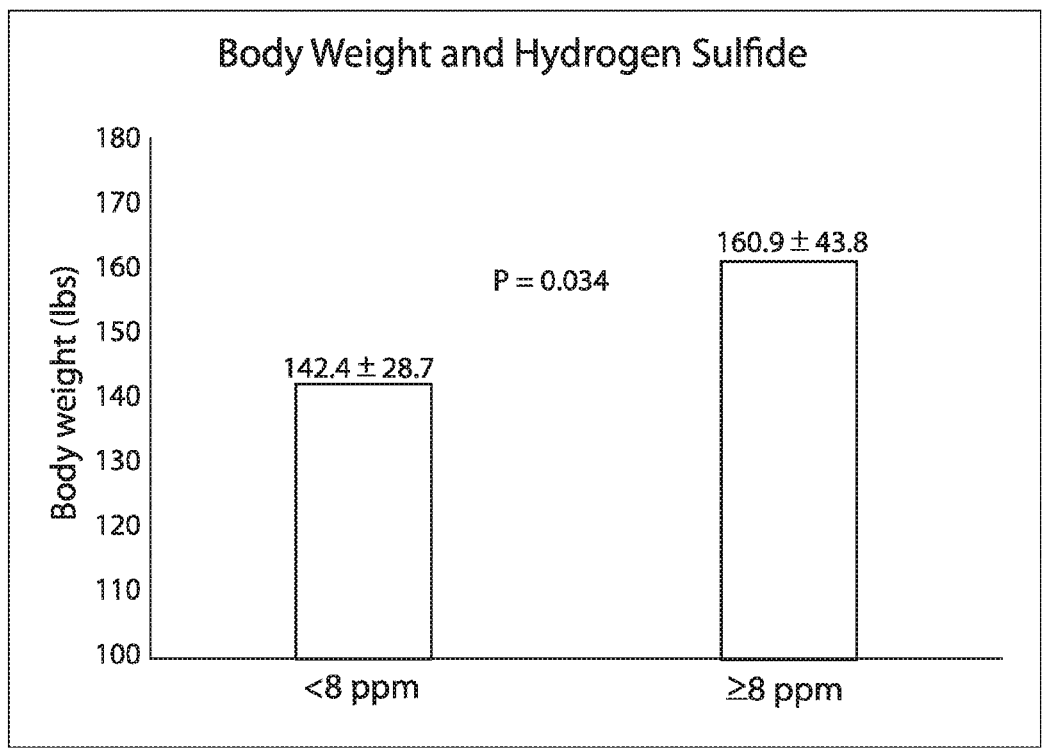
FIG. 9 depicts body weight in relation to hydrogen sulfide concentration. It also appears that higher production of $H_2S$ is associated with greater BMI using an 8 ppm cutoff for AUC.
Figure 10:
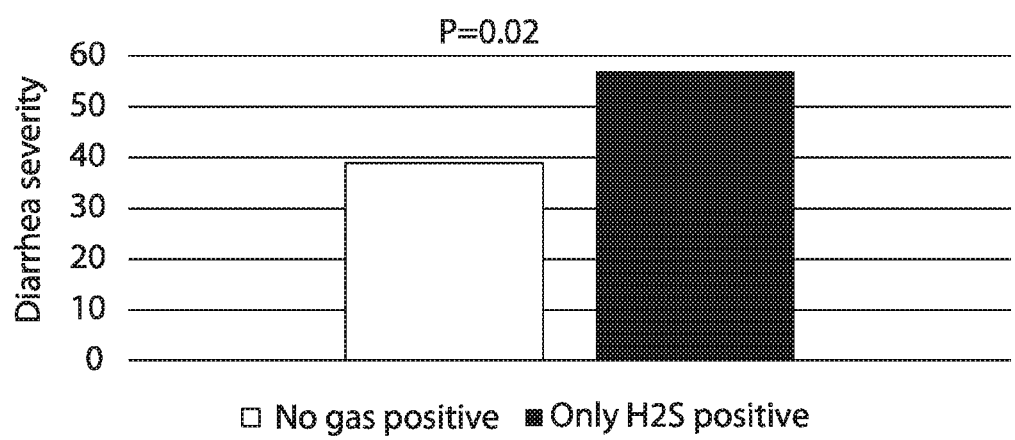
FIG. 10 depicts $H_2S$ only on breath test versus none positive. In this graph, the presence of only $H_2S$ on the breath of ≥1.2 ppm peak, was associated with diarrhea again. This time in a larger cohort of subjects. The $H_2S$ only subjects were compared to normal breath test subjects.
Figure 11:
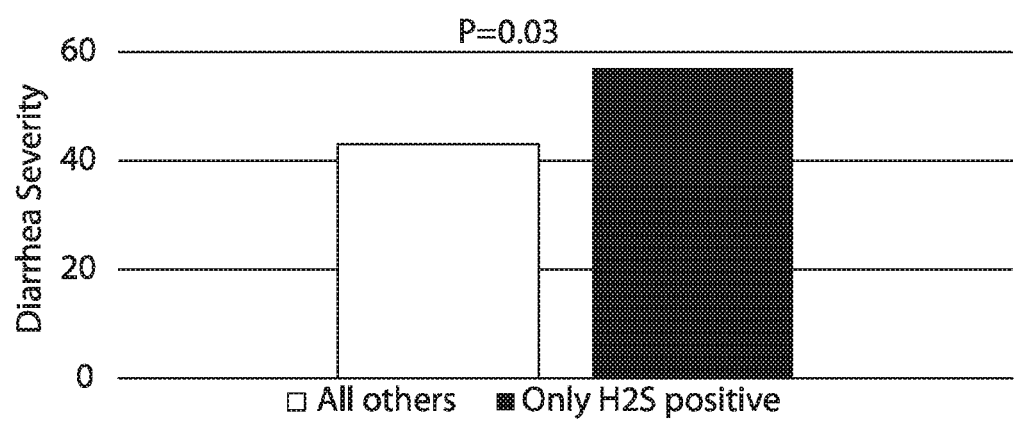
FIG. 11 depicts $H_2S$ only on breath test versus all others. Here the $H_2S$ only subjects were compared to all other subjects and again, diarrhea is statistically greater.
Figure 12:
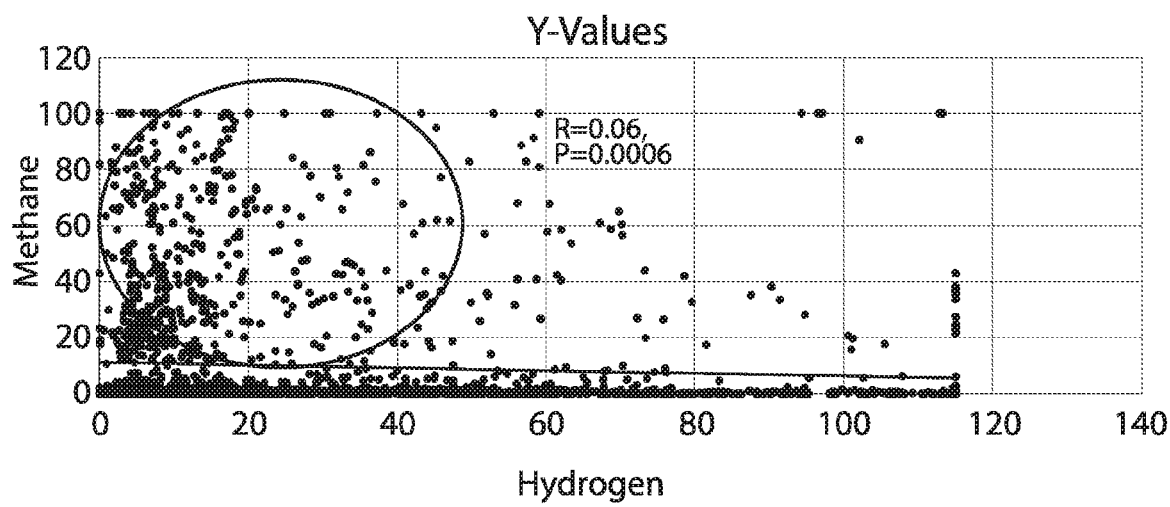
FIG. 12 shows that higher methane lower hydrogen. This figure demonstrates that at higher $CH_4$ levels from breath, there is lower hydrogen in line with the $CH_4$ consuming hydrogen to produce $CH_4$.
Figure 13:
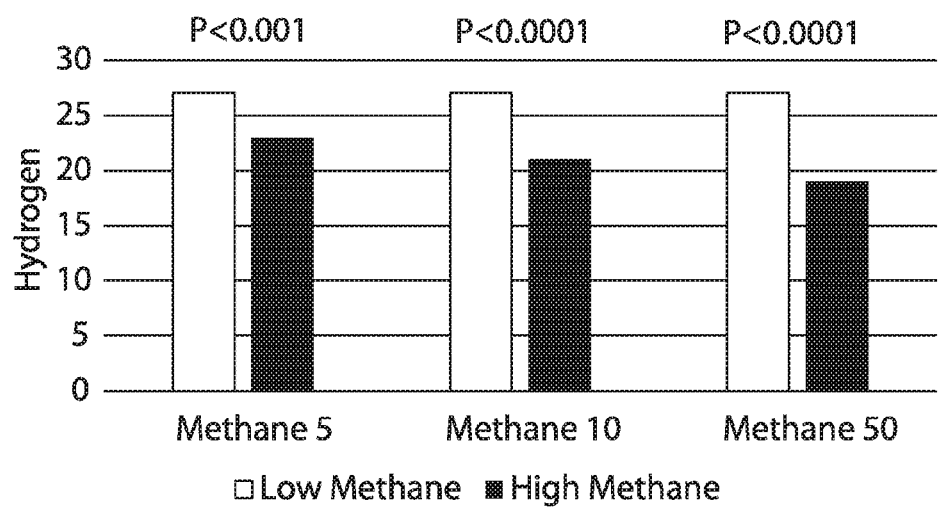
FIG. 13 shows that hydrogen depends on methane. The dependence of $CH_4$ on hydrogen is shown more explicitly in strata of $CH_4$ levels detected in breath. The greater the peak $CH_4$ the more $H_2$ is suppressed.
Figure 14:
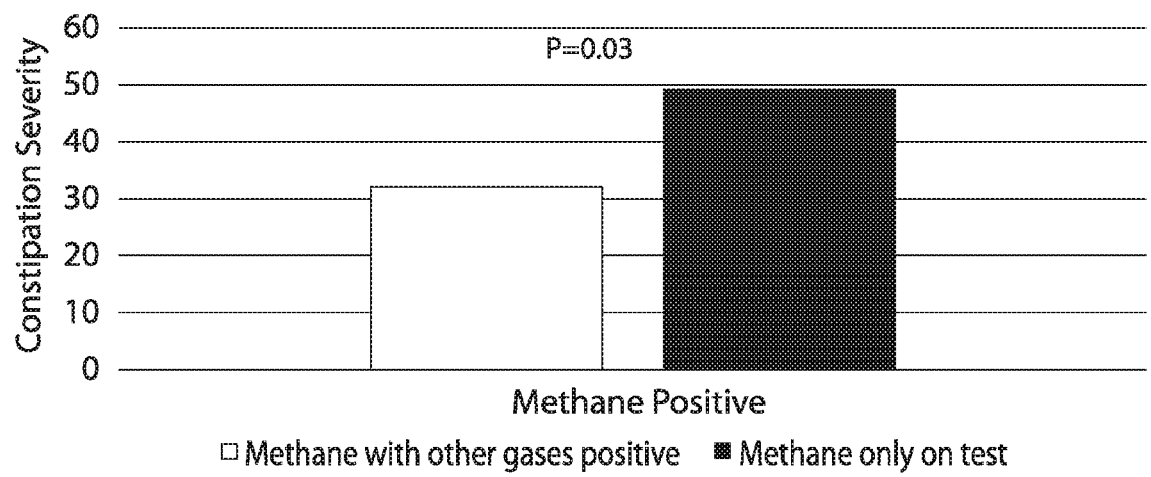
FIG. 14 depicts methane and constipation. In this figure, when methane is the sole gas produced in high peak amounts (≥10 ppm), subjects are more constipated than methane when other gases are competing and present.
Figure 15:
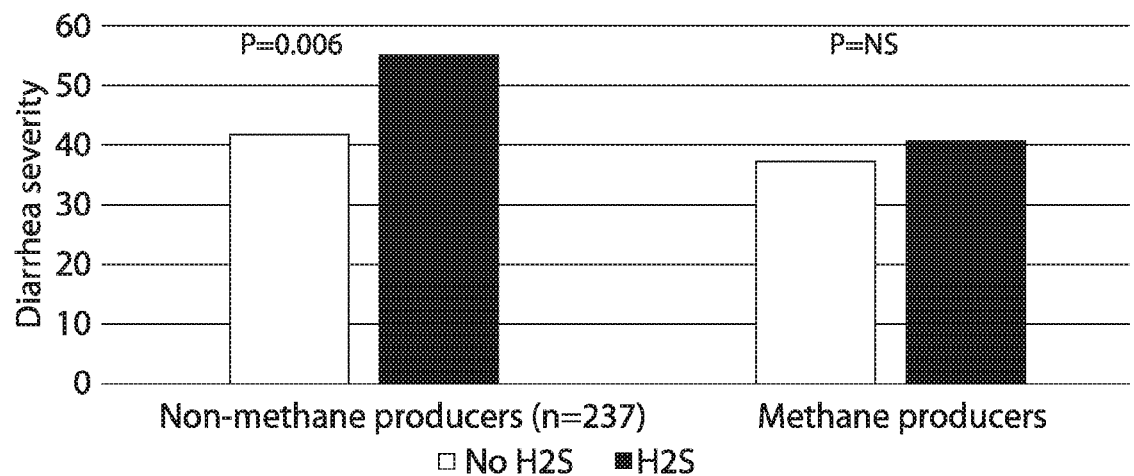
FIG. 15 depicts diarrhea (Effect of hydrogen sulfide). In the analysis of the larger cohort of patients, once again $H_2S$ is seen to cause diarrhea. However, in the panel on the right, $CH_4$ overpowers $H_2S$ to neutralize the effect ($CH_4$ is constipating and $H_2S$ is diarrhea producing and they cancel).
Figure 16:
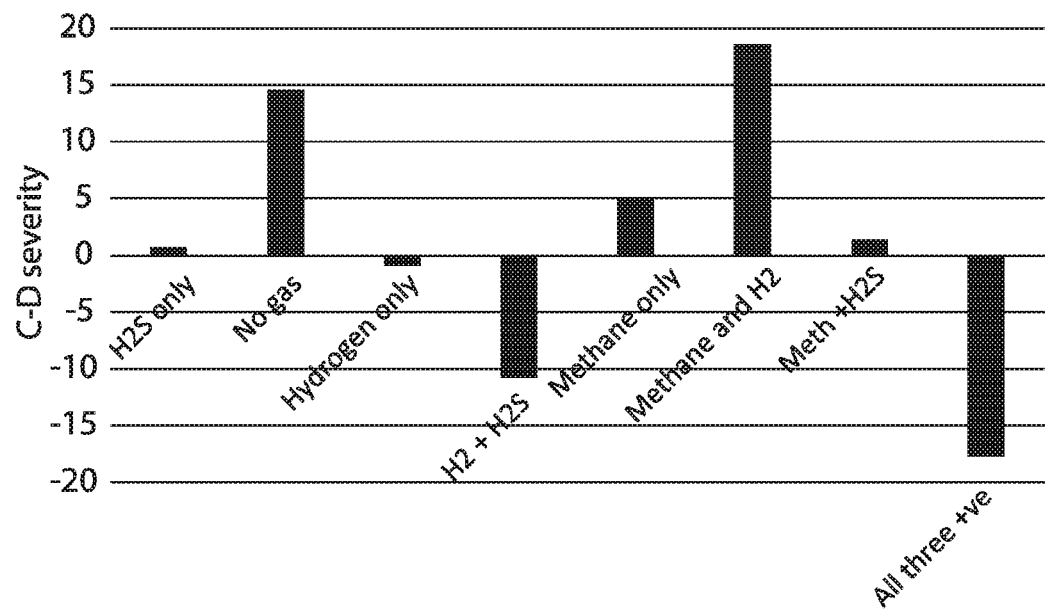
FIG. 16 depicts constipation-diarrhea vs gas type. This is depiction based on determining the push and pull effect of diarrhea and constipation. In this figure, the diarrhea severity on a scale of 0-100 mm is subtracted from the constipation severity on the same scale. A positive number implies constipation is winning. A negative number that diarrhea is winning. Clearly, $CH_4$ is associated with constipation and $H_2S$ leans in favor of diarrhea unless $CH_4$ is there which is almost 0 (balanced).

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., Revised, J. Wiley & Sons (New York, NY. 2006); March, *Advanced Organic Chemistry Reactions, Mechanisms and Structure* 7$^{th}$ ed., J. Wiley & Sons (New York, NY 2013); and Sambrook and Russel, *Molecular Cloning: A Laboratory Manual* 4$^{th}$ ed., Cold Spring Harbor Laboratory Press (Cold Spring Harbor, NY 2012), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

"Beneficial results" may include, but are in no way limited to, lessening or alleviating the severity of the disease condition, preventing the disease condition from worsening, curing the disease condition and prolonging a patient's life or life expectancy.

"Mammal" as used herein refers to any member of the class Mammalia, including, without limitation, humans and nonhuman primates such as chimpanzees, and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus adult, child and newborn subjects, whether male or female, are intended to be including within the scope of this term.

Selecting a therapy as used herein, includes but is not limited to selecting, choosing, prescribing, advising, recommending, instructing, or counseling the subject with respect to the treatment.

"Therapeutically effective amount" as used herein refers to that amount which is capable of achieving beneficial results in a patient with a disease or condition. A therapeutically effective amount can be determined on an individual basis and will be based, at least in part, on consideration of the physiological characteristics of the mammal, the type of delivery system or therapeutic technique used and the time of administration relative to the progression of the disease.

"Treatment" and "treating," as used herein refer to both therapeutic treatment and prophylactic or preventative measures, wherein the object is to prevent, slow down and/or lessen the disease even if the treatment is ultimately unsuccessful.

Described herein is the first clinical examination of detectable $H_2S$ in human BTs in North America. Without wishing to be bound by any particular theory, the inventors believe that $H_2S$ is an important missing link to SIBO, as $H_2S$ is herein found to be bioactive and like methane is important in predicting clinical symptoms such as diarrhea and fatigue. Embodiments of present invention are based, at least in part, on these findings.

$H_2S$ Positive SIBO

Various embodiments of the present invention provide for a method of treating hydrogen sulfide ("$H_2S$") positive small intestinal bacterial overgrowth ("SIBO"), comprising: administering a treatment for $H_2S$ positive SIBO to a subject who has been diagnosed with $H_2S$ positive SIBO. In various embodiments, the method further comprises identifying a subject who has $H_2S$ positive SIBO before administering the treatment. In particular embodiments, the treatment is rifaximin.

Various embodiments of the present invention provide for a method of treating hydrogen sulfide ("$H_2S$") positive small intestinal bacterial overgrowth ("SIBO"), comprising: administering rifaximin to treat $H_2S$ positive SIBO in a subject who has been diagnosed with $H_2S$ positive SIBO. In various embodiments, the method further comprises identifying a subject who has $H_2S$ positive SIBO before administering the treatment.

Various embodiments of the present invention provide for a method of treating hydrogen sulfide ("$H_2S$") positive small intestinal bacterial overgrowth ("SIBO"), comprising: administering a treatment for $H_2S$ positive SIBO to a subject who has been diagnosed with $H_2S$ positive SIBO by a method comprising: obtaining a biological sample from the subject; measuring the hydrogen sulfide ($H_2S$) level in the biological sample; and diagnosing $H_2S$ positive SIBO if the $H_2S$ level is higher than a reference level.

Various embodiments of the present invention provide for a method of treating hydrogen sulfide ("$H_2S$") positive small intestinal bacterial overgrowth ("SIBO"), comprising: administering rifaximin to treat $H_2S$ positive SIBO to a subject who has been diagnosed with $H_2S$ positive SIBO by a method comprising: obtaining a biological sample from the subject; measuring the hydrogen sulfide ($H_2S$) level in the biological sample; and diagnosing $H_2S$ positive SIBO if the $H_2S$ level is higher than a reference level.

Various embodiments of the present invention provide for a method of treating $H_2S$ positive SIBO, comprising: requesting a test result obtained from a method comprising: obtaining a biological sample from the subject, measuring the hydrogen sulfide ($H_2S$) level in the biological sample, and diagnosing $H_2S$ positive SIBO if the $H_2S$ level is higher than a reference level; and administering a treatment for $H_2S$ positive SIBO to the subject who has been diagnosed with $H_2S$ positive SIBO.

Various embodiments of the present invention provide for a method of diagnosing $H_2S$ positive SIBO, comprising: obtaining a biological sample from a subject; measuring the hydrogen sulfide ($H_2S$) level in the biological sample; and diagnosing $H_2S$ positive SIBO if the $H_2S$ level is higher than a reference level.

Various embodiments of the present invention provide for a method for selecting a therapy for a subject, comprising: obtaining a biological sample from a subject; measuring the hydrogen sulfide ($H_2S$) level in the biological sample; and selecting a therapy for $H_2S$ positive SIBO if the $H_2S$ level is higher than a reference level.

Various embodiments of the present invention provide a method for selecting a subject for a clinical trial, comprising: obtaining a biological sample from a subject; measuring the hydrogen sulfide ($H_2S$) level in the biological sample; and selecting the subject for a clinical trial for the treatment of $H_2S$ positive SIBO if the $H_2S$ level is higher than a reference level.

The reference level used in various embodiments of the present invention are described in more detail below.

Diarrhea

Various embodiments of the present invention provide for a method of diagnosing diarrhea, comprising: obtaining a biological sample from a subject; measuring the hydrogen sulfide ($H_2S$) level in the biological sample; and diagnosing diarrhea if the $H_2S$ level is higher than a reference level.

Various embodiments of the present invention provide for a method for selecting a therapy for a subject, comprising: obtaining a biological sample from a subject; measuring the hydrogen sulfide ($H_2S$) level in the biological sample; and selecting a therapy for diarrhea if the $H_2S$ level is higher than a reference level.

Various embodiments of the present invention provide a method for selecting a subject for a clinical trial, comprising: obtaining a biological sample from a subject; measuring the hydrogen sulfide ($H_2S$) level in the biological sample; and selecting the subject for a clinical trial for the treatment of diarrhea if the $H_2S$ level is higher than a reference level.

Various embodiments of the present invention provide for a method of treating diarrhea, comprising: administering a treatment for diarrhea to a subject who has been diagnosed with diarrhea by a method comprising: obtaining a biological sample from the subject; measuring the hydrogen sulfide ($H_2S$) level in the biological sample; and diagnosing diarrhea if the $H_2S$ level is higher than a reference level.

Various embodiments of the present invention provide for a method of treating $H_2S$ positive diarrhea, comprising: administering a treatment to a subject diagnosed with $H_2S$ positive diarrhea. In various embodiments, the method comprises identifying the subject with $H_2S$ positive diarrhea before administering treatment.

Various embodiments of the present invention provide for a method of treating $H_2S$ positive diarrhea, comprising: administering a treatment for $H_2S$ positive diarrhea to a subject who has been diagnosed with $H_2S$ positive diarrhea by a method comprising: obtaining a biological sample from the subject; measuring the hydrogen sulfide ($H_2S$) level in the biological sample; and diagnosing diarrhea if the $H_2S$ level is higher than a reference level.

Various embodiments of the present invention provide for a method of treating diarrhea, comprising: requesting a test result obtained from a method comprising: obtaining a biological sample from the subject, measuring the hydrogen sulfide ($H_2S$) level in the biological sample, and diagnosing diarrhea if the $H_2S$ level is higher than a reference level; and administering a treatment for diarrhea to the subject who has been diagnosed with diarrhea.

Various embodiments of the present invention provide for a method of treating $H_2S$ positive diarrhea, comprising: requesting a test result obtained from a method comprising: obtaining a biological sample from the subject, measuring the hydrogen sulfide ($H_2S$) level in the biological sample, and diagnosing $H_2S$ positive diarrhea if the $H_2S$ level is higher than a reference level; and administering a treatment for $H_2S$ positive diarrhea to the subject who has been diagnosed with diarrhea.

In various embodiments, the treatment is rifaximin.

The reference level used in various embodiments of the present invention are described in more detail below.

Abdominal Pain

Various embodiments of the present invention provide for a method of diagnosing $H_2S$ positive abdominal pain, comprising: obtaining a biological sample from a subject; measuring the hydrogen sulfide ($H_2S$) level in the biological sample; and diagnosing $H_2S$ positive abdominal pain if the $H_2S$ level is higher than a reference level.

Various embodiments of the present invention provide for a method for selecting a therapy for a subject, comprising: obtaining a biological sample from a subject; measuring the hydrogen sulfide ($H_2S$) level in the biological sample; and selecting a therapy for $H_2S$ positive abdominal pain if the $H_2S$ level is higher than a reference level.

Various embodiments of the present invention provide a method for selecting a subject for a clinical trial, comprising: obtaining a biological sample from a subject; measuring the hydrogen sulfide ($H_2S$) level in the biological sample; and selecting the subject for a clinical trial for the treatment of $H_2S$ positive abdominal pain if the $H_2S$ level is higher than a reference level.

Various embodiments of the present invention provide for a method of treating $H_2S$ positive abdominal pain, comprising: administering a treatment for $H_2S$ positive abdominal pain to a subject who has been diagnosed with $H_2S$ positive abdominal pain by a method comprising: obtaining a biological sample from the subject; measuring the hydrogen sulfide ($H_2S$) level in the biological sample; and diagnosing $H_2S$ positive abdominal pain if the $H_2S$ level is higher than a reference level.

Various embodiments of the present invention provide for a method of treating $H_2S$ positive abdominal pain, comprising: administering a treatment to a subject diagnosed with $H_2S$ positive abdominal pain. In various embodiments, the method comprises identifying the subject with $H_2S$ positive abdominal pain before administering treatment.

Various embodiments of the present invention provide for a method of treating $H_2S$ positive abdominal pain, comprising: administering a treatment for $H_2S$ positive abdominal pain to a subject who has been diagnosed with $H_2S$ positive abdominal pain by a method comprising: obtaining a biological sample from the subject; measuring the hydrogen sulfide ($H_2S$) level in the biological sample; and diagnosing $H_2S$ positive abdominal pain if the $H_2S$ level is higher than a reference level.

Various embodiments of the present invention provide for a method of treating $H_2S$ positive abdominal pain, comprising: requesting a test result obtained from a method comprising: obtaining a biological sample from the subject, measuring the hydrogen sulfide ($H_2S$) level in the biological sample, and diagnosing $H_2S$ positive abdominal pain if the $H_2S$ level is higher than a reference level; and administering a treatment for $H_2S$ positive abdominal pain to the subject who has been diagnosed with $H_2S$ positive abdominal pain.

In various embodiments, the treatment is rifaximin.

The reference level used in various embodiments of the present invention are described in more detail below.

Urgency

Various embodiments of the present invention provide for a method of diagnosing likelihood of having bowel urgency, comprising: obtaining a biological sample from a subject; measuring the hydrogen sulfide ($H_2S$) level in the biological sample; and diagnosing the subject as having bowel urgency if the $H_2S$ level is higher than a reference level.

Various embodiments of the present invention provide for a method for selecting a therapy for a subject, comprising: obtaining a biological sample from a subject; measuring the hydrogen sulfide ($H_2S$) level in the biological sample; and selecting a therapy for having bowel urgency if the $H_2S$ level is higher than a reference level.

Various embodiments of the present invention provide a method for selecting a subject for a clinical trial, comprising: obtaining a biological sample from a subject; measuring the hydrogen sulfide ($H_2S$) level in the biological sample; and selecting the subject for a clinical trial for the treatment bowel urgency if the $H_2S$ level is higher than a reference level.

Various embodiments of the present invention provide for a method of treating bowel urgency, comprising: administering a treatment for bowel urgency to a subject who has been diagnosed with having $H_2S$ positive bowel urgency. In various embodiments, the method comprises first identifying the subject who has $H_2S$ positive bowel urgency before administering treatment.

Various embodiments of the present invention provide for a method of treating bowel urgency, comprising: administering a treatment for bowel urgency to a subject who has been diagnosed with having bowel urgency by a method comprising: obtaining a biological sample from the subject; measuring the hydrogen sulfide ($H_2S$) level in the biological sample; and diagnosing bowel urgency if the $H_2S$ level is higher than a reference level.

Various embodiments of the present invention provide for a method of treating bowel urgency, comprising: requesting a test result obtained from a method comprising: obtaining a biological sample from the subject, measuring the hydrogen sulfide ($H_2S$) level in the biological sample, and diagnosing bowel urgency if the $H_2S$ level is higher than a reference level; and administering a treatment for bowel urgency to the subject who has been diagnosed with bowel urgency.

In various embodiments, the treatment is rifaximin.

The reference level used in various embodiments of the present invention are described in more detail below.

Fatigue

Various embodiments of the present invention provide for a method of diagnosing fatigue, comprising obtaining a biological sample from a subject; measuring the hydrogen sulfide ($H_2S$) level in the biological sample; and diagnosing fatigue if the $H_2S$ level is higher than a reference level.

Various embodiments of the present invention provide for a method for selecting a therapy for a subject, comprising: obtaining a biological sample from a subject; measuring the hydrogen sulfide ($H_2S$) level in the biological sample; and selecting a therapy for fatigue if the $H_2S$ level is higher than a reference level.

Various embodiments of the present invention provide for a method for selecting a subject for a clinical trial, comprising: obtaining a biological sample from a subject; measuring the hydrogen sulfide ($H_2S$) level in the biological sample; and selecting the subject for a clinical trial for the treatment of fatigue if the $H_2S$ level is higher than a reference level.

Various embodiments of the present invention provide for a method of $H_2S$ positive treating fatigue, comprising: administering a treatment for $H_2S$ positive fatigue to a subject who has been diagnosed with $H_2S$ positive fatigue. In various embodiments, the method comprises identifying the subject with $H_2S$ positive fatigue before administering treatment.

Various embodiments of the present invention provide for a method of treating fatigue, comprising: administering a treatment for fatigue to a subject who has been diagnosed with fatigue by a method comprising: obtaining a biological sample from the subject; measuring the hydrogen sulfide ($H_2S$) level in the biological sample; and diagnosing fatigue if the $H_2S$ level is higher than a reference level.

Various embodiments of the present invention provide for a method of treating fatigue, comprising: requesting a test result obtained from a method comprising: obtaining a biological sample from the subject; measuring the hydrogen sulfide ($H_2S$) level in the biological sample, and diagnosing fatigue if the $H_2S$ level is higher than a reference level; administering a treatment for fatigue to the subject who has been diagnosed with fatigue.

In various embodiments, the treatment is rifaximin.

The reference level used in various embodiments of the present invention are described in more detail below.

Detection of $H_2S$

Various embodiments of the present invention provide for a method of detecting $H_2S$ in a subject having or suspected of having a condition selected from the group consisting of SIBO, diarrhea, bowel urgency, fatigue, irritable bowel syndrome (IBS), diarrhea predominant IBS (D-IBS), constipation predominant IBS (C-IBS), and combinations thereof, comprising: obtaining a biological sample from the subject having or suspected of having the condition; and measuring the hydrogen sulfide ($H_2S$) level in the biological sample. Prior to the present invention, it was not known that $H_2S$ can be bioactive and cause diarrhea, bowel urgency, or fatigue and thus, patients having or suspected of having these conditions did not have a reason to test for $H_2S$ to see if their condition was caused by $H_2S$.

Subjects

The subject from whom a biological sample is obtained can be a subject who has or is suspected to have a disease or condition caused, at least in part, by having high $H_2S$ levels. Examples of these subjects include but are not limited to those who are or who are suspected to have small intestinal bacterial overgrowth (SIBO), irritable bowel syndrome (IBS), diarrhea predominant IBS (D-IBS), constipation predominant IBS (C-IBS), diarrhea, bowel urgency, fatigue, constipation, bloating, diabetes, or obesity. In various embodiments, the subject is a human subject.

In certain embodiments, the subject from whom a biological sample is obtained can be a subject who desires to know whether he or she is susceptible to a disease or condition caused, at least in part, by having high $H_2S$ levels. Examples of these subjects include but are not limited to those who desire to know whether he or she is susceptible to having SIBO, irritable bowel syndrome (IBS), D-IBS, C-IBS, diarrhea, bowel urgency, fatigue, constipation, bloating, diabetes, or obesity.

Reference Levels

In various embodiments, wherein the biological sample is a breath sample, the reference level for $H_2S$ is 6 parts per million (ppm). In various embodiments, wherein the biological sample is a breath sample, the reference level for $H_2S$ is 8 parts per million (ppm). In various embodiments, wherein the biological sample is a breath sample, the reference level for $H_2S$ is 1.2 parts per million (ppm). In other embodiments, wherein the biological sample is breath, the reference level for $H_2S$ is 1 ppm, 2 ppm, 3 ppm, 4 ppm, 5 ppm, 7 ppm, 8 ppm, 9 ppm, or 10 ppm.

The reference level can depend on the type of disease or condition that will be determined, as well as the sensitivity of the detection method or system. Different reference levels can be set for different diseases or conditions and for different detection methods and systems.

In some embodiments, the reference level can be established from biological samples from a healthy subject. For example, if the biological sample is breath, then the reference level can be obtained from the breath of a healthy subject. In other embodiments, the reference level is the average $H_2S$ level for the same type of biological sample from a population of healthy subjects. In other embodiments, the reference level is the average plus one or two standard deviations of average $H_2S$ level for the same type of biological sample from a population of healthy subjects. In some embodiments, the population of healthy subjects can range from at least three healthy individuals to 25 healthy individuals, to 50 healthy subject, 75 healthy subject, and even more than 100 healthy individuals. In various embodiments, a healthy subject is a subject who on questionnaire, report no altered bowel function, no bloating and no abdominal pain (each less than 10 mm on a 100 mm VAS scale for the specific symptom).

In certain embodiments, wherein breath samples are taken, and methane and/or hydrogen are also measured, the methane reference value can be about 3 ppm or about 5 ppm and the hydrogen reference value can be about 20 ppm.

Biological Samples

In various embodiments, the biological sample is a breath sample. Examples of other biological samples include but are not limited to body fluids, whole blood, plasma, serum, stool, intestinal fluids or aspirate, and stomach fluids or aspirate, serum, breath, cerebral spinal fluid (CSF), urine, sweat, saliva, tears, pulmonary secretions, breast aspirate, prostate fluid, seminal fluid, cervical scraping, amniotic fluid, intraocular fluid, mucous, and moisture in breath. In particular embodiments of the method, the biological sample may be whole blood, blood plasma, blood serum, stool, intestinal fluid or aspirate or stomach fluid or aspirate, or stool. In various embodiments, the biological sample may be whole blood. In various embodiments, the biological sample may be serum. In various embodiments, the biological sample may be plasma. In various embodiments, the biological sample may be stool.

Breath Test

In various embodiments, $H_2S$ can be detected and measured via breath testing. In various embodiments the breath test can utilize (1) sorbent based technology; and/or (2) membrane based technology to measure the levels of gases exhaled by a subject.

One potential technology to measure the gas levels includes certain sorbent technologies. In general, these are substances that absorb gases. In order to measure a gas concentration using sorbents, the sorbents can be first weighed, then exposed to the gas. After exposure, the sorbents can be weighed again to determine the increase from the added mass of the absorbed gas. Alternatively, the change in mass may be measured by other means such as luminescence, color, transparency, conductivity, or resonance.

The following formula may be utilized to determine the concentration of $H_2$ in exhaled breath gases based on weighing the sorbents:

$$\frac{V_{Lung}}{V_{per\ mol\ of\ air}} * C_{H_2} = N_{H_2}$$

$$\frac{5\ L}{24\frac{L}{mol}} * 1\ ppm = 2 \times 10^{-7}\ mol$$

$$N_{H_2} * M_{Hydrogen} = Total\ Weight_{Hydrogen\ per\ breath}$$

$$2 \times 10^{-7}\ mol * 1\frac{g}{mol} * 2 = 4 \times 10^{-7}\ g = .4\ \mu g\ (per\ .3)$$

Where:
V—Volume (litres)
C—Concentration
N—Number of mots (per breath)
M—Molecular mass of hydrogen atoms (grams)

$CO_2$ (40000 ppm), $H_2S$ (1 ppm) and methane (1 ppm) can be calculated in a similar manner and require scales sensitive to 0.6 g, 6 pg, and 3 pg respectively. Technology such as a quartz crystal microbalance may be utilized to detect weights to that level of precision.

In some embodiments, sorbent materials may require a resetting process after each use to expel all of the absorbed gases. For instance, some sorbents require a heating cycle to force the sorbent to release the stored gas, or some similar process. In other embodiments, a sorbent material may be selected which rapidly releases the absorbed gases. Accordingly, devices utilizing sorbents may include a heating element or other processing technology that would be triggered after each use to expel the gases. In other embodiments, the sorbents may be disposed of and replaced instead of being reset, but would need to be mounted to the weight measurement device.

Types of sorbents that may be utilized include immobilized amine, aminosilane, and organoclay sorbents. The amine sorbents, for example, may be regenerable. Some examples of suitable sorbents include high performance hollow microspheres, hollow fibers and supported liquid membranes. Specifically, the high performance hollow microspheres include amine microspheres. In one example, the hollow microspheres may be made of biocompatible materials for use in medical applications. The hollow microspheres have geometries that allow for detection of several gases. Further, the organoclay sorbents may be used for $CO_2$ and $H_2S$ detection. In one example, the organoclay sorbent may be an amine based sorbent. Some sorbents are designed to be regenerable such that the modified amine is regenerated in the presence of water vapor.

Examples of sorbent based technology and methods used for detecting gases are described in, for example, U.S. Pat. No. 8,500,854, issued on Aug. 6, 2013, titled Regenerable Sorbent Technique for Capturing $CO_2$ using Immobilized Amine Sorbents, and U.S. Pat. No. 7,288,126, issued on Oct. 30, 2007, titled High Capacity Immobilized Amine Sorbents, both of which are incorporated by reference herein in their entirety.

In some embodiments, membrane based technology may be utilized to determine the concentrations of breath gases. For instance, membranes could first be utilized to selectively filter gases of interest. Then, another sensor technology may determine the concentration of the isolated gas that has permeated through the other side of the membrane. For example, pressure sensors (to detect partial pressure changes), gas chromatography, or a simple counter could be utilized. In some embodiments, the combination of membranes with other sensor technologies may enhance the selectivity of the device.

Some examples of membranes to be incorporated into the devices and methods disclosed herein include flat sheet membranes, hollow microspheres and mixed matrix membranes. Mixed matrix membranes, in particular, may be advantageous as they have different levels of bulk and surface porosity as well as customizable inner and outer diameter dimensions. The geometries of the membranes allow for maximum detection of several gases. Specifically, mixed matrix membranes with metal organic frameworks may be used for detection of $CO_2$ and $CH_4$.

Breath $H_2S$ test is based fermentative bacteria found in the gastrointestinal tract producing detectable quantities of $H_2S$ as fermentation products from a substrate consumed by the host, under certain circumstances. Substrates include sugars such as lactulose, xylose, lactose, glucose, or fructose. The $H_2S$ produced in the small intestine then enters the blood stream of the host and are gradually exhaled.

Typically, after an overnight fast, the patient swallows a controlled quantity of a sugar, such as lactulose, xylose, lactose, glucose, or fructose and breath samples are taken at frequent time intervals, typically every 10 to 15 minutes for a two- to four-hour period. In certain embodiments, samples are analyzed by gas chromatography or by other suitable techniques, singly or in combination. In other embodiments, samples are analyzed using a sorbent based technology and/or membrane based technology as described herein.

In various embodiments, the breath test can be performed utilizing a device or method as described in International Application Publication No. WO 2017/040546, herein incorporated by reference as though fully set forth.

$H_2S$ Test

In other embodiments, $H_2S$ can be detected and measured from $H_2S$ production in a biological sample, such as stool.

For example, $H_2S$ can be measured over a period of time of fermentation from the biological sample. Exemplarily fermentation periods include but are not limited to 0.25, 0.5, 0.75, 1.0, 1.25, 1.5, 1.75, 2.0, 2.5, 3.0, 3.5, 4.0, 4.5, 5.0, 6.0, 7.0, or 8.0 hours.

Therapies

In various embodiments, once a high $H_2S$ level is detected (e.g., above 1.2 ppm, above 6 ppm, or above 8 ppm in a breath test, depending on which cut-off is used), a therapy aimed at lowering the $H_2S$ level can be selected or administered to the subject.

In various embodiments, a therapy for the treatment of diarrhea can be selected or administered to the subject.

In various embodiments, a therapy for the treatment of fatigue can be selected or administered to the subject.

In various embodiments an antibiotic or a combination of two or more antibiotics can be selected and/or administered to subjects who have a $H_2S$ level higher than the reference level. Examples of antibiotics include but are not limited to aminoglycosides (e.g., amikacin, gentamicin, kanamycin, neomycin, netilmicin, streptomycin, tobramycin, paromomycin), ansamycins (e.g., geldanamycin, herbimycin), carbacephems (e.g., loracarbef), carbapenems (e.g., ertapenem, doripenem, imipenem, cilastatin, meropenem), cephalosporins (e.g., first generation: cefadroxil, cefazolin, cefalotin or cefalothin, cefalexin; second generation: cefaclor, cefamandole, cefoxitin, cefprozil, cefuroxime; third generation: cefixime, cefdinir, cefditoren, cefoperazone, cefotaxime, cefpodoxime, ceftazidime, ceftibuten, ceftizoxime, ceftriaxone; fourth generation: cefepime; fifth generation: ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins (e.g., amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin), antibiotic polypeptides (e.g., bacitracin, colistin, polymyxin b), quinolones (e.g., ciprofloxacin, enoxacin, gatifloxacin, levofloxacin, lomefloxacin, moxifloxacin, norfloxacin, ofloxacin, trovafloxacin), rifamycins (e.g., rifampicin or rifampin, rifabutin, rifapentine, rifaximin), sulfonamides (e.g., mafenide, prontosil, sulfacetamide, sulfamethizole, sulfanilamide, sulfasalazine, sulfisoxazole, trimethoprim, trimethoprim-sulfamethoxazole (co-trimoxazole, "tmp-smx"), and tetracyclines (e.g., demeclocycline, doxycycline, minocycline, oxytetracycline, tetracycline) as well as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin combination, and tinidazole.

In various embodiments, the antibiotic selected, or directed and/or administered is rifaximin. The rifaximin therapy selected, directed and/or administered can be 200-2400 mg/dose, administered two or three times per day. In various embodiments the dosage can be about 50, 75, 100, 125, 150, 175, 200, 250, 300, 350, 400, 450, 500, 550, 600, 650, or 700 mg/dose. In particular embodiments, the dosage can be about 550 mg/dose. In various embodiments, the rifaximin therapy can be administered one, two, three, four or five times a day. In various embodiments, the therapy can be administered for 5, 7, 10, 14, 15, 20, 21, or 28 days. In various embodiments, the therapy can be re-administered after a period of no therapy.

In various embodiments, the antibiotic selected and/or administered is neomycin. The neomycin therapy selected, directed and/or administered can be 500-1000 mg/dose, administered two times per day. In various embodiments the dosage can be about 100, 200, 300, 400, 500, 600, 700, 750, 1000, 1100, 1200, 1300, 1400, or 1500 mg/dose. In various embodiments, the neomycin therapy can be administered one, two, three, four or five times a day. In various embodiments, the therapy can be administered for 5, 7, 10, 14, 15, 20, 21, or 28 days. In various embodiments, the therapy can be re-administered after a period of no therapy.

In various embodiments, the antibiotic selected and/or administered is vancomycin. The vancomycin therapy selected, directed, and/or administered can be about 125 mg/dose, administered four times per day. In various embodiments the dosage can be about 50, 75, 100, 125, 150, 175, 200, 250, 300, 350, 400, 450, or 500 mg/dose. In various embodiments, the vancomycin can be administered one, two, three, four or five times a day. In various embodiments, the therapy can be administered for 5, 7, 10, 14, 15, 20, 21, or 28 days. In various embodiments, the therapy can be re-administered after a period of no therapy.

In various embodiments, the antibiotic selected and/or administered is metronidazole. The metronidazole therapy selected, directed and/or administered can be 250-500 mg/dose, administered three times per day. In various embodiments the dosage can be about 50, 75, 100, 125, 150, 175, 200, 250, 300, 350, 400, 450, 500, 550, 600, 650, 700, 800, 900, or 1000 mg/dose. In various embodiments, the metronidazole therapy can be administered one, two, three, four or five times a day. In various embodiments, the therapy can be administered for 5, 7, 10, 14, 15, 20, 21, or 28 days. In various embodiments, the therapy can be re-administered after a period of no therapy.

Particularly effective antibiotics may be non-absorbable antibiotics. Examples of non-absorbable antibiotics include but are not limited to rifaximin, neomycin, Bacitracin, vancomycin, teicoplanin, ramoplanin, and paramomycin.

In some embodiments, a probiotic agent that inhibits the growth of $H_2S$ producing microorganisms can be selected or administered, for example, *Bifidobacterium* sp. or *Lactobacillus* species or strains, e.g., *L. acidophilus, L. rhamnosus, L. plantarum, L. reuteri, L. paracasei* subsp. *paracasei*, or *L. casei Shirota*, or probiotic *Saccharomyces* species, e.g., *S. cerevisiae*, is selected and/or administered. In some embodiments, the agent that inhibits the growth of $H_2S$ producing microorganisms can be methanogens or acetogens. These microorganisms can compete with the growth of $H_2S$ producing microorganisms and thus inhibit the growth and proliferation of $H_2S$ producing microorganisms. The methanogen can be from the genus *Methanobrevibacter*. Examples of *Methanobrevibacter* include but are not limited to *M. acididurans, M. arboriphilus, M. curvatus, M. cuticularis, M. filiformis, M. gottschalkii, M. millerae, M. olleyae, M. oxalis, M. ruminantium, M. smithii, M. thaueri, M. woesei*, and *M. wolinii*. In certain embodiments, the *Methanobrevibacter* is *Methanobrevibacter smithii* (*M. Smithii*). The agent that inhibits the growth of $H_2S$ producing microorganisms can be typically administered in a pharmaceutically acceptable ingestible formulation, such as in a capsule, or for some subjects, consuming a food supplemented with the inoculum is effective, for example a milk, yoghurt, cheese, meat or other fermentable food preparation. These probiotic agents can inhibit the growth of $H_2S$ producing microorganisms, for example, by competing against $H_2S$ producing microorganisms for growth and thus reduce or inhibit the growth of $H_2S$ producing microorganisms.

In various embodiments, the present invention provides pharmaceutical compositions including a pharmaceutically acceptable excipient along with a therapeutically effective amount of a therapeutic agent. "Pharmaceutically acceptable excipient" means an excipient that is useful in preparing a pharmaceutical composition that is generally safe, nontoxic, and desirable, and includes excipients that are acceptable for veterinary use as well as for human pharmaceutical use. Such excipients may be solid, liquid, semisolid, or, in the case of an aerosol composition, gaseous.

In certain embodiments, the compounds of the present invention may contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals such as sodium, lithium, potassium, calcium, magnesium and the like, as well as nontoxic ammonium, quaternary ammonium, and amine cations including, but not limited to ammonium, tetramethylanunonium, tetraethyl ammonium, methyl amine, dimethyl amine, trimethylamine, triethylamine, ethylamine, and the like (see, e.g., Berge S. M., et al. (1977) J. Pharm. Sci. 66, 1).

The term "pharmaceutically acceptable esters" refers to the relatively nontoxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

As used herein, "pharmaceutically acceptable salts or prodrugs" are salts or prodrugs that are, within the scope of sound medical judgment, suitable for use in contact with the tissues of subject without undue toxicity, irritation, allergic response, and the like, commensurate with a reasonable benefit/risk ratio, and effective for their intended use.

The term "prodrug" refers to compounds that are rapidly transformed in vivo to yield the functionally active one or more peptides as disclosed herein or a mutant, variant, analog or derivative thereof. A thorough discussion is provided in T. Higachi and V. Stella, "Pro-drugs as Novel Delivery Systems," Vol. 14 of the A. C. S. Symposium Series, and in Bioreversible Carriers in: Drug Design, ed. Edward B. Roche, American Pharmaceutical Association and Pergamon Press, 1987, both of which are hereby incorporated by reference. As used herein, a prodrug is a compound that, upon in vivo administration, is metabolized or otherwise converted to the biologically, pharmaceutically or therapeutically active form of the compound. A prodrug of the one or more peptides as disclosed herein or a mutant, variant, analog or derivative thereof can be designed to alter the metabolic stability or the transport characteristics of one or more peptides as disclosed herein or a mutant, variant, analog or derivative thereof, to mask side effects or toxicity, to improve the flavor of a compound or to alter other characteristics or properties of a compound. By virtue of knowledge of pharmacodynamic processes and drug metabolism in vivo, once a pharmaceutically active form of the one or more peptides as disclosed herein or a mutant, variant, analog or derivative thereof, those of skill in the pharmaceutical art generally can design prodrugs of the compound (see, e.g., Nogrady (1985) Medicinal Chemistry A Biochemical Approach, Oxford University Press, N. Y., pages 388-392). Conventional procedures for the selection and preparation of suitable prodrugs are described, for example, in "Design of Prodrugs," ed. H. Bundgaard, Elsevier, 1985. Suitable examples of prodrugs include methyl, ethyl and glycerol esters of the corresponding acid.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Transdermal" administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Via the parenteral route, the compositions may be in the form of solutions or suspensions for infusion or for injection. Via the topical route, the pharmaceutical compositions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indication. Via the ocular route, they may be in the form of eye drops. The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. For additional guidance, see *Remington: The Science and Practice of Pharmacy* (Gennaro ed. 20th edition, Williams & Wilkins PA, USA) (2000).

Typical dosages can be in the ranges recommended by the manufacturer where known therapeutic compounds are used. Such dosages typically can be reduced by up to about one order of magnitude in concentration or amount without losing the relevant biological activity. Thus, the actual dosage can depend upon the judgment of the physician, the condition of the patient, and the effectiveness of the therapeutic method based, for example, on the in vitro responsiveness in a biological sample, or the responses observed in the appropriate animal models.

Kits

The present invention is also directed to a kit to diagnose diarrhea or fatigue by detecting $H_2S$ levels. The kit is useful for practicing the inventive method that involves the measurement of $H_2S$. The kit is an assemblage of materials or components. Thus, in some embodiments the kit contains a composition including a substrate as described above for use in a breath test. In other embodiments, the kit contains a composition including a therapy for use in treating the $H_2S$ positive diseases or conditions.

The exact nature of the components configured in the inventive kit depends on its intended purpose. For example, some embodiments are configured for the purpose of $H_2S$ detection in humans. In one embodiment, the kit is configured particularly for the purpose of treating mammalian subjects. In further embodiments, the kit is configured for veterinary applications, treating subjects such as, but not limited to, farm animals, domestic animals, and laboratory animals.

Instructions for use may be included in the kit. "Instructions for use" typically include a tangible expression describing the technique to be employed in using the components of the kit to effect a desired outcome, such as to measure the level of $H_2S$. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well-known methods, preferably to provide a sterile, contaminant-free environment. As used herein, the term "package" refers to a suitable solid matrix or material such as glass, plastic, paper, foil, and the like, capable of holding the individual kit components. The packaging material generally has an external label which indicates the contents and/or purpose of the kit and/or its components.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Consecutive patients undergoing BTs at a tertiary care motility program were consented. For the BT, subjects presented after a 24 hour-preparation, beginning with 12-hour diet restrictions and a subsequent 12-hour fast. After a baseline breath sample, 10 g of lactulose or 25 g of fructose was administered, followed by collection of breath samples every 15 minutes for 120 minutes. Breath samples were then analyzed on a Quintron Breathtracker™ gas chromatograph (Quintron Diagnostics, Milwaukee, WI) to measure $H_2$ and $CH_4$ after correction for $CO_2$. Remaining breath samples in the collection bag were analyzed for detectable $H_2S$ (Alphasense, Essex, UK). Patients completed a questionnaire evaluating gastrointestinal symptoms, medical history, and demographics. The AUC of $H_2S$ over 120 minutes was used to determine the relevant clinical cutoffs. This was then compared to symptom severity by non-parametric testing and multivariate analysis to rule out effect of age and gender.

A total of 101 subjects were recruited for this study with 99 studies (62% female, mean age=46.2±16.3 years, 98 of these were lactulose test) having complete data on $H_2S$ measurements. For the entire group the mean AUC for $H_2S$ was 5.37±2.29 ppm (range=2.57-16.44 ppm). Using a sensitivity analysis, a significant relationship was seen between the level of $H_2S$ and specific symptoms. For diarrhea, AUC levels of $H_2S \geq 6.0$ were associated with greater severity of diarrhea (P=0.028, see table). The same cutoff was notable for a greater degree of fatigue in the high $H_2S$ category (P=0.035). Interestingly, the $H_2$ AUC was higher in the high $H_2S$ group (367±232 ppm) compared to the low $H_2S$ group (244±176 ppm) (P=0.02) consistent with $H_2$ consumption to produce $H_2S$ by sulfate-reducing bacteria. Age and gender were not confounding variables in this analysis.

TABLE 1

Comparison of AUC 120 for hydrogen sulfide to symptoms during breath testing

| Symptom | Low $H_2S$ (<6.0 ppm) | High $H_2S$ (>6.0 ppm) | P-value |
|---|---|---|---|
| Diarrhea | 48.1 ± 33.1 | 63.5 ± 24.5 | 0.028 |
| Constipation | 53.1 ± 31.2 | 63.5 ± 24.4 | 0.20 |
| Abdominal Pain | 59.9 ± 27.8 | 69.1 ± 19.4 | 0.16 |
| Fatigue | 61.6 ± 31.2 | 79.2 ± 14.7 | 0.04 |

Example 1B 127 patients were recruited from GI Motility Program of Cedars-Sinai Medical Center. Subjects ≥18 years undergoing lactulose breath testing were eligible to participate in this study. Subjects prepared with standard-of-care diet restriction and fast. Baseline breath sample was taken; then ingestion of 10 g lactulose was done; then collection of breath samples were performed every 15 mins for 120 mins.

Patients completed questionnaire during 120-minute breath test collection: Gastrointestinal symptoms, Medical/surgical history, Demographics.

Statistical Analyses: $H_2S$ levels were assessed by examining the AUC 120 or maximum $H_2S$ during the first 120 minutes of testing; Chi-squared ($\chi 2$) test was used for comparisons of qualitative data; Nonparametric analyses were used for non-normal data Comparisons; Spearman's rank correlation was applied in the comparison of interquartile assessment of $H_2S$ levels.

TABLE 2

Demographics
H2S Cutoff

| | <8 ppm (n = 77) | ≥8 ppm (n = 50) | P-value |
|---|---|---|---|
| Age (years) | 46.2 ± 16.8 | 53.6 ± 16.7 | P = 0.02 |
| Gender (% female) | 64.9 | 80.3 | P = 0.07 |

$H_2S$ is important in breath testing and correlates with patient symptoms ≥8 ppm AUC or ≥1.2 ppm max appears to be initial candidate cut-offs for patient symptoms. $H_2S$ and $CH_4$ appear competitive. $H_2S$ can be an important gas to be assessed in relation to the gut microbiome.

Example 2

Figure 18:
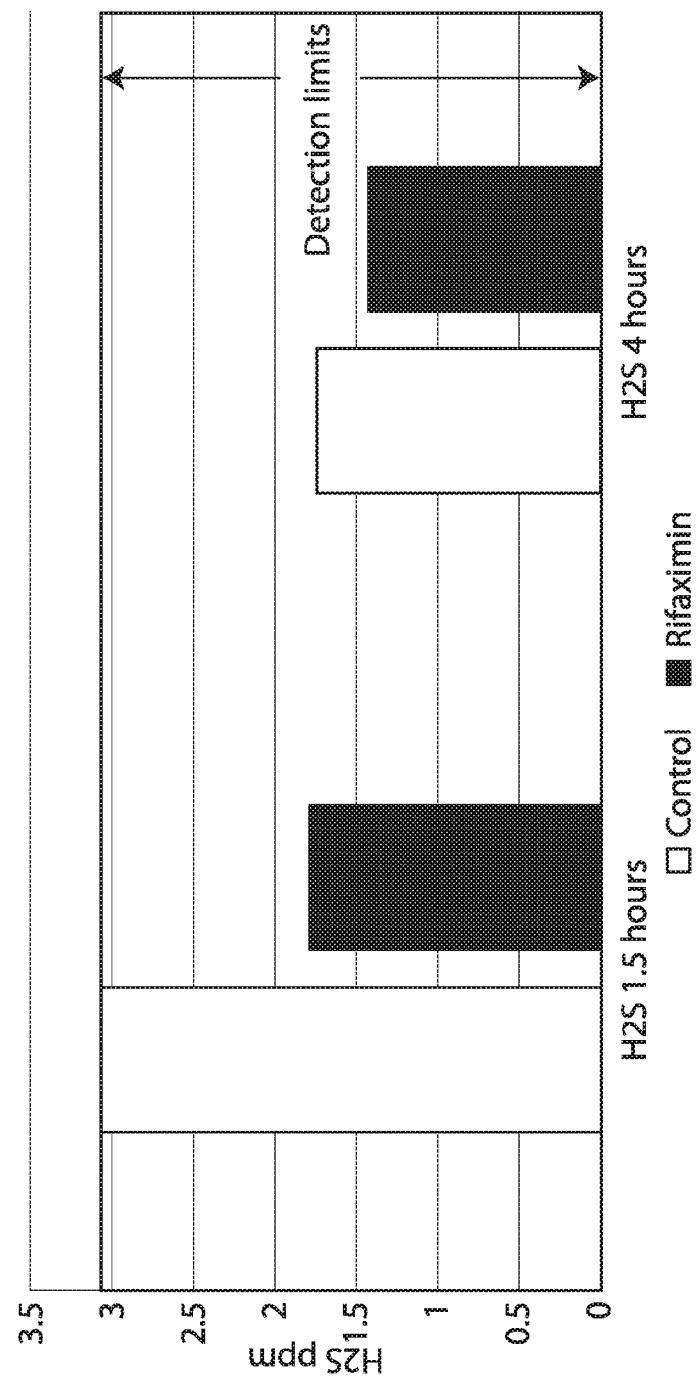
FIG. 18 depicts the effects of rifaximin on $H_2S$. In this figure, fresh stool was used to assess $H_2S$ over 1.5 and 4 hours of fermentation with or without the addition of the antibiotic rifaximin. In this graph, it is clear that rifaximin reduces $H_2S$ production.

The effects of rifaximin on $H_2S$ was examined. Fresh stool was used to assess $H_2S$ over 1.5 and 4 hours of fermentation with or without the addition of the antibiotic rifaximin. As shown in FIG. 18, it is clear that rifaximin reduces $H_2S$ production.

Example 3

4-Gas Device for Breath Testing Shows Exhaled $H_2S$ is Associated with Diarrhea and Abdominal Pain in a Large Scale Prospective Trial Adult subjects undergoing routine lactulose breath testing at a tertiary outpatient clinic were consented for the study. Subjects underwent a 24-hour pre-test preparation, following a specific diet for the first 12 hours and fasting for the remaining 12. Subjects provided a baseline breath sample and, after consuming 10 g lactulose dissolved in 250 mL water, successive breath samples were collected every 15 minutes over the next 120 minutes. Each breath sample was analyzed using a 4-gas device, simultaneously measuring $H_2$, $CH_4$, $CO_2$, and $H_2S$. Subjects completed a questionnaire evaluating medical history, demographics, and severity of gastrointestinal symptoms (0-100 mm VAS scale). The gas profiles were then related to the presence and severity of symptoms.

Of the 300 subjects who consented for the study, 298 had complete data for analysis. Based on $H_2$ alone, breath testing was positive for SIBO in 182 (61%) subjects. Diarrhea severity was not different between those with (44.2±2.4) and without $H_2$ (43.2±3.0) (P=0.79). The range of $H_2S$ levels in these subjects was 0.43 to 1.99 ppm. Using a sensitivity analysis, $H_2S$ was associated with more diarrhea and the cutoff for this discrimination was a maximum level of 1.2 ppm at any point during the test. Using this cutoff, 72 subjects (24.2%) were positive for $H_2S$. Diarrhea severity in $H_2S$ subjects was 52.1±3.8 compared to 41.2±2.1 in non-$H_2S$ subjects (P=0.01). In some cases, $H_2S$ was positive in addition to $H_2$ and/or $CH_4$. However, the greatest severity of diarrhea was seen in subjects with $H_2S$ only (≥1.2 ppm). Similarly, subjects with excess $H_2S$ but normal $CH_4$ and $H_2$ had greater abdominal pain (71.1±5.1) than normal breath test patients (52.9±3.8). In fact, the greatest abdominal pain was seen in subjects positive for $H_2S$ only (P<0.05).

In this large-scale trial, the 4-gas device for breath testing demonstrates the importance of $H_2S$ in diarrhea and abdominal pain. Despite the lack of correlation between $H_2$ and these two symptoms, subjects positive for $H_2S$ only (≥1.2 ppm) had the greatest diarrhea and abdominal pain among subjects referred for testing. This finding is important as it complements the breath test panel for MO testing and can be a predictor for treatment.

Example 4

Competitive Hydrogen Gas Utilization by Methane- and Hydrogen Sulfide-Producing Microorganisms and Associated Symptoms: Results of a 4-Gas Breath Test Machine Breath testing subjects at a tertiary care center were consented. After fasting, subjects provided a baseline breath sample, consumed 10 g lactulose, and gave breath samples every 15 min for 120 min. $H_2$, $CH_4$, $H_2S$, and $CO_2$ levels were measured using the 4-gas detection device. Subjects completed a medical history, demographics, and symptoms questionnaire. Diarrhea, bloating, constipation, and abdominal pain severity were measured using 0-100 mm VAS scales. Positive breath testing was based on the North American consensus for $H_2$ (≥20 ppm at or before 90 min) and $CH_4$ (≥10 ppm during 120 min). Sensitivity analysis found $H_2S \geq 1.2$ ppm at any point was clinically important.

Competition for $H_2$ utilization was assessed by $CH_4$ and $H_2S$. $CH_4$ and $H_2S$ levels were also correlated with symptoms.

Figure 17:
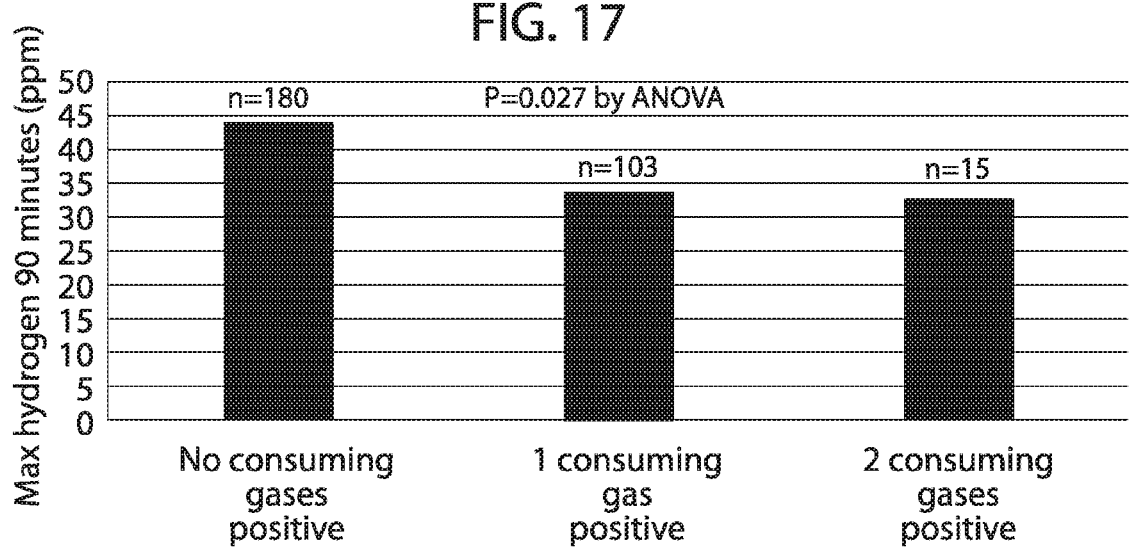
FIG. 17 depicts Proof of Hydrogen Consumption Total group. Compared methane and hydrogen sulfide pooled (n=118) and all other non-consumers. In this figure, the $H_2$ level is assessed based on whether is one ($H_2S$ or $CH_4$) or two ($H_2S$ and $CH_4$) present on the breath test. The greater number of competing gases means lower $H_2$ as it is being used.

Of 300 subjects enrolled, 298 had complete data (mean age=49.0±1.0 yrs; 66% female). Among these, 8 distinct patterns were noted with 238 (80%) subjects positive for at least one gas. Of these, 25 subjects who would have been categorized as non-$CH_4$/non-$H_2$ (i.e. flat-liners) were positive for $H_2S$. Excess $CH_4$ production was associated with lower $H_2$ levels (32.2±4.3 ppm) compared to normal $CH_4$ (60.1±2.7 ppm; P<0.0001). After excluding $CH_4$-positive subjects, $H_2$ levels were lower in subjects with excess $H_2S$ (34.8±3.7 ppm) compared to those with normal $H_2S$ (60.1±2.7 ppm; P<0.0001). $H_2$ was also lower in $CH_4$-positive subjects (32.0±8.1 ppm) compared to excess $H_2S$ producers (34.8±3.7 ppm; P=0.81). $H_2$ levels were successively lower when comparing no consuming gases, one consuming gas ($CH_4$ or $H_2S$), and two consuming gases ($CH_4$ and $H_2S$) (FIG. 17) (ANOVA, p<0.05). $CH_4$-positive subjects, irrespective of other gas present, had a constipation-predominant pattern. $H_2S$-positive subjects exhibited a diarrhea-predominant pattern.

This 4-gas device can assess a more complete interaction of fermented gases in breath testing. This study shows that $CH_4$ and $H_2S$ are independently associated with lower $H_2$, consistent with the known physiology of $CH_4$ and $H_2S$ production via $H_2$ consumption. For the first time, we demonstrate the dynamics between competing gases in terms of dominant symptom manifestation (diarrhea vs. constipation).

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

What is claimed is:

1. A method for selecting a therapy for a subject, and treating the subject, comprising:
    obtaining a biological sample from a subject;
    measuring the hydrogen sulfide ($H_2S$) level in the biological sample during a test;
    selecting a therapy for an $H_2S$ positive condition when the $H_2S$ level is higher than 1.2 ppm cut-off at any point during the test; and
    administering the selected therapy to the subject to treat the $H_2S$ positive condition, wherein the $H_2S$ therapy comprises rifaximin,
    wherein the $H_2S$ positive condition is selected from the group consisting of $H_2S$ positive diarrhea, $H_2S$ positive fatigue, $H_2S$ positive bowel urgency, $H_2S$ positive abdominal pain and combinations thereof,
    wherein the biological sample is a breath sample.

2. The method of claim 1, wherein the subject has or is suspected of having irritable bowel syndrome.

3. The method of claim 1, wherein $H_2S$ is measured using a four gas detection device or system and the four gases are $H_2$, $CH_4$, $H_2S$, and $CO_2$.

4. The method of claim 1, wherein $H_2S$ is measured after the subject ingests a controlled quantity of a substrate selected from the group consisting of lactulose, xylose, lactose, glucose, fructose and combinations thereof.

* * * * *